(12) United States Patent
Ramstack et al.

(10) Patent No.: US 8,809,492 B2
(45) Date of Patent: Aug. 19, 2014

(54) METHOD FOR FABRICATING NANOPARTICLES

(71) Applicant: Cerulean Pharma Inc., Cambridge, MA (US)

(72) Inventors: J. Michael Ramstack, Lunenburg, MA (US); John Podobinski, Boston, MA (US)

(73) Assignee: Cerulean Pharma Inc., Cambridge, MA (US)

( * ) Notice: Subject to any disclaimer, the term of this patent is extended or adjusted under 35 U.S.C. 154(b) by 0 days.

(21) Appl. No.: 14/023,227

(22) Filed: Sep. 10, 2013

(65) Prior Publication Data

US 2014/0010724 A1    Jan. 9, 2014

Related U.S. Application Data

(63) Continuation of application No. 13/357,977, filed on Jan. 25, 2012, now Pat. No. 8,546,521.

(60) Provisional application No. 61/437,142, filed on Jan. 28, 2011.

(51) Int. Cl.
*C08G 75/02*    (2006.01)
*C08F 6/12*    (2006.01)

(52) U.S. Cl.
USPC ........ 528/499; 210/195.2; 210/196; 422/187; 522/450; 977/840

(58) Field of Classification Search
USPC ............... 210/195.2, 196; 422/187; 522/450; 977/840
See application file for complete search history.

(56) References Cited

U.S. PATENT DOCUMENTS

| | | | |
|---|---|---|---|
| 3,267,074 A | 8/1966 | Wood | |
| 3,286,992 A | 11/1966 | Ameniades et al. | |
| 4,511,258 A | 4/1985 | Federighi et al. | |
| 5,049,322 A | 9/1991 | Devissaguet et al. | |
| 5,118,528 A | 6/1992 | Fessi et al. | |
| 5,650,173 A | 7/1997 | Ramstack et al. | |
| 5,654,008 A | 8/1997 | Herbert et al. | |
| 5,869,103 A | 2/1999 | Yeh et al. | |
| 5,945,126 A | 8/1999 | Thanoo et al. | |
| 6,331,317 B1 | 12/2001 | Lyons et al. | |
| 6,338,859 B1 | 1/2002 | Leroux et al. | |
| 6,395,304 B2 | 5/2002 | Lyons et al. | |
| 6,407,079 B1 | 6/2002 | Muller et al. | |
| 6,634,825 B2 | 10/2003 | Tolkoff et al. | |
| 6,638,994 B2 | 10/2003 | Crooks et al. | |
| 6,705,757 B2 | 3/2004 | Lyons et al. | |
| 6,939,033 B2 | 9/2005 | Lyons et al. | |
| 6,942,767 B1 | 9/2005 | Fazzina et al. | |
| 6,998,051 B2 | 2/2006 | Chattopadhyay et al. | |
| 7,147,806 B2 | 12/2006 | Castor | |
| 7,179,484 B2 | 2/2007 | Singh | |
| 7,270,808 B2 | 9/2007 | Cheng et al. | |
| 7,300,671 B2 | 11/2007 | Lyons et al. | |
| 7,495,052 B2 | 2/2009 | Raiche et al. | |
| 7,504,088 B2 | 3/2009 | Riley et al. | |
| 7,510,730 B2 | 3/2009 | Lyons et al. | |
| 7,550,441 B2 | 6/2009 | Farokhzad et al. | |
| 7,811,605 B2 | 10/2010 | Moro et al. | |
| 2002/0142017 A1 | 10/2002 | Simonnet | |
| 2004/0091546 A1 | 5/2004 | Johnson et al. | |
| 2007/0122440 A1 | 5/2007 | Macosko et al. | |
| 2007/0156266 A1 | 7/2007 | Jensen et al. | |
| 2007/0158266 A1 | 7/2007 | Shekunov et al. | |
| 2007/0282034 A1 | 12/2007 | Patel et al. | |
| 2008/0081074 A1 | 4/2008 | Gu et al. | |
| 2008/0193518 A1 | 8/2008 | Zarkadas et al. | |
| 2008/0248126 A1 | 10/2008 | Cheng et al. | |
| 2009/0169635 A1 | 7/2009 | Schwarz et al. | |
| 2009/0324552 A1 | 12/2009 | Lichter et al. | |
| 2010/0104655 A1 | 4/2010 | Zale et al. | |
| 2010/0152077 A1 | 6/2010 | Allston et al. | |
| 2010/0210465 A1 | 8/2010 | Li et al. | |
| 2011/0237748 A1 | 9/2011 | Podobinski et al. | |

FOREIGN PATENT DOCUMENTS

| | | |
|---|---|---|
| WO | 9741837 | 11/1997 |
| WO | 02078674 | 10/2002 |
| WO | 2007127380 | 11/2007 |
| WO | 2008070270 | 6/2008 |
| WO | 2009095448 | 8/2009 |
| WO | 2010005721 | 1/2010 |
| WO | 2010005723 | 1/2010 |

(Continued)

OTHER PUBLICATIONS

Anton et al. "Design and Production of Nanoparticles Formulated From Nano-Emulsion Templates—A Review", J. Control Release, Jun. 24, 2008;128(3):185-99. Epub Feb. 23, 2008.

(Continued)

*Primary Examiner* — Terressa Boykin
(74) *Attorney, Agent, or Firm* — Pepper Hamilton LLP; Thomas J. Engellenner; Reza Mollaaghababa

(57) ABSTRACT

Systems and methods are provided for filtering a fluid containing nanoparticles. The systems and methods generally include introducing a stream of the nanoparticle-containing fluid into a holding vessel, and extracting at least a part of a nanoparticle-containing fluid accumulated in the holding vessel. The extracted nanoparticle-containing fluid is passed through a filtration module to separate a nanoparticle-containing retentate from a permeate, and the retentate is returned to the vessel. The filtration cycle can be repeated until a desired concentration of the nanoparticles is achieved in the holding vessel. In many embodiments, the generation of the nanoparticle-containing fluid and its filtration are performed concurrently.

21 Claims, 3 Drawing Sheets

(56) References Cited

FOREIGN PATENT DOCUMENTS

| | | |
|---|---|---|
| WO | 2010005726 | 1/2010 |
| WO | 2010036211 | 4/2010 |
| WO | 2010114770 | 10/2010 |

OTHER PUBLICATIONS

Aqil et al., "Preparation of Stable Suspensions of Gold Nanoparticles in Water by Sonoelectrochemistry", Ultrason Sonochem, Sep. 2008; 15(6):1055-61, Epub Apr. 22, 2008.
Aumelas et al.. "Nanoparticles of Hydrophobically Modified Dextrans as Potential Drug Carrier Systems", Colloids Surf B Biointerfaces, Sep. 1, 2007;59(1): 74-80, Epub May 3, 2007.
Balazs et al., "Nanoparticle Polymer Composites: Where Two Small Worlds Meet", Science, vol. 314, pp. 1107-1110, (2006).
Bilati et al., "Development of a Nanoprecipitation Method Intended for the Entrapment of Hydrophillic Drugs Into Nanoparticles", European Journal of Pharmaceutical Sciences, vol. 24, pp. 67-75, (2005).
Bouchemal et al,, "Simultaneous Emulsification and Interfacial Polycondensation for the Preparation of Colloidal Suspensions of Nanocapsules", Materials Science and Engineering: C, vol. 26, No. 2-3, pp. 472-480 (2005).
Bourne et al., "Micromixing and Fast Chemical Reactions in STatic Mixers", Chem. Eng. Process, vol. 30, pp. 23-30 (1991).
Brigger et al., "Nanoparticles in Cancer Therapy and Diagnosis", Advanced Drug Delivery Reviews, vol. 54, pp. 631-651, (2002).
Cai et al. "Charged Nanoparticles as Protein Deilvery Systems: A Feasibility Study Using Lysozyme as Model Protein", Eur. J. Pharm. Biopharm., May; 69(1):31-42, Epub Oct. 12, 2007.
Cheng et al., "Stablizier-Free Poly(lactide-co-glycolide) Nanoparticles for Multimodal Biomedical Probes", Biomater vol. 29, No. 13, ISSN: 0142-9612, pp. 2104-2112 (2008).
Cheng et al., "A Microscal Multi-Inlet Vortex Nanoprecipitation Reactor: Turbulence Measurement and Simulation", Applied Physics Letters, vol. 94, pp. 204104-1 through 204014-3.
Chognot et al. "Surfactive Water-Soluble Copolymers for the Preparation of Controlled Surface Nanoparticles by Double Emulsion/ Solvent Evaporation", Colloids Surf B Bio interfaces, Oct. 1;59(2): 194-207, Epub May 18, 2007.
Choi et al., "Thermodynamic Parameters on poly(d,l-lactide-co-glycolide) Particle Size in Emulsification-Diffusion Process", Colloids and Surfaces A: Physicohemical and Engineering Aspects Vo. 201, pp. 283-289 (2002).
Dalwadi et al., "Purification of PEGylated Nanoparticles Using Tangential Flow Filtration (TFF)", Drug Dev Ind Pharm, Sep;33(4):1030-9.
Dong et al., "Methoxy poly(ethlene glycol)-poly(lactide) (MPEG-PLA) Nanoparticles for Controlled Delivery of Anticancer Drugs", Biomaterials, Jun. 2004;25(14):2843-9.
Dong et al., "Encapsulation of Lipophilic Drugs Within Enteric Micropartiles by a Novel Coacervation Method", Int J. Pharm. Dec. 1, 2006;326(1-2):128-38, Epub Jul. 15, 2006.
Dong et al., "Poly(D,L-lactide-co-glycolide) (PLGA) Nanoparticles Prepared by High Pressure Homogenization for Paclitaxel Chemotherapy", Int J Pharm Sep. 5, 2007;342(1-2):208-14, Epub May 6, 2007.
Dong et all., "A Continuous and Highly Effective Static Mixing Process for Antisolvent Precipitation of Nanoparticles of Poorly Water-Soluble Drugs", International Journal of Pharmaceutics, 386(1) pp. 256-261, Nov. 13, 2009.
Douroumis et al., "Enhanced Dissolution of Oxcarbazepine Microcrystals Using a Static Mixer Process", Science Direc vol. 59, pp. 208-214, (2007).
Douroumis et al., "Using a Modified Shepards Method for Optimization of a Nanoparticulate Cyclosporine A Formulation Prepared by a Static Mixer Technique", Journal of Pharmaceutical Sciences; vol. 97. No. 2, pp. 919-930 (2008).

Fessi et al. "Nanocapsule Formation ByInterfacial Polymer Deposition Follwoing Solvent Displacement", Inernational Journal of Pharmaceutics vol. 55, R1-R4, (1989).
Freitas et al., "Solvent Extraction Employing a Static Micromixer: A Simple, Robust and Versatile Technology for the Microencapsulation of Proteins", Journal of Microencapsulation vol. 20, No. 1, pp. 67-85, (2003).
Galindo-Rodriguez et al., "Physicochemical Parameters Associated With Nanoparticle Formation in the Salting-Out, Emulsification-Diffusion, and Nanoprecipitation Methods", Pharmaceutical Research, vol. 21, No. 8, pp. 1428-1439, (2004).
Galindo-Rodriguez et al. "Comparative Scale-Up of Three Mehtods for Producing Ibuprofen-loaded Nanoparticles", European Journal of Pharmaceutical Sciences Vo. 25, pp. 357-367 (2005).
Ganachaud et al. Nanoparticles and Nanocapsule Created Using The Ouzo Effect: Spontaneous Emulsification as an Alternative to Ul;trasonic and High-Shea Devices; ChemPhysChem vol. 6, pp. 209-216 (2005).
Gindy et al., Composite Block Copolymer Stabilized Nanoparticles; Simultaneous Encapsulation of Organic Actives and Inorganic Nanostructures, Langmuir, vol. 24, pp. 83-90, American Chemical Society (2008).
Gindy et al. "Preparation of poly(ethylene glycol) Proteted Nanoparticles With Varible Bioconjugate Ligand Density", Biomacromolecules vol. 9, pp. 2705-2711,American Chemical Society (2008).
Govender et al., "PLGA Nanoparticles Prepared by Nanoprecipitation: Drug Loading and Release Studies of a Water Soluble Drug", Journal of Controlled Release, vol. 57, pp. 171-185 (1999).
Hans et al., "Biodegradable Nanoparticles for Drug Delivery and Targeting", Current Opinion in Solid Sate and Materials Science pp. 319-327, Philadelphia, PA, (2002).
Her et al., "Continuous Precipitation of Monodispersed Colloidal Particles", Journal of Materials Research, pp. 156-161 (1996).
Horn et al., "Organic Nanoparticles in the Aqueous Phase", Theory, Experiment, and Use, Angew, , Chem. Int Ed. pp. 4330-4361, (2001).
Hornig et al., "Synthetic Polymeric Nanoparticles by Nanoprecipitation", J. Mater. Chem., 19, pp. 3838-3840 (2009).
International Search Report and Written Opinion dated May 24, 2011 for PCT/US2011/024062.
Jobmann et al., "Submicronpartiles from Biodegradable Polymers", International Journal of Pharmaceutics, Vo. 242, pp. 213-217 (2002).
Johnson et al,, "Flash Nanoprecipitation of Organic Actives and Block Copolymers Using a confined Impinging Jets Mixer", Aust. J. Chem. vol. 56, pp. 1021-1024, (2003).
Karnik et al., "Microfluidic Platform for Controlled Synthesis of Polymeric Nanoparticles", Nano Letters, vol. 8, No. 9, pp. 2906-2912, (2008).
Legrand et al., "Influence of Polymer Behaviour in Organic Solution on the Production of Polylactide Nanoparticles by Nanoprecipitation", Int J. Pharm. Nov. 1, 2007;344 (1-2):33-43. Epub May 31, 2007.
Lemarchand et al., "Polysaccharide-decoarted Nanoparticles", Eur J Pharm Biopharm. 582):327-41, Sep. 2004.
Leo et al., "Nanoparticle Formulation May Affect the Stabilization of an Antilschemic Prodrug", Int J. Pharm, Jan. 3, 2006;307(1):103-13, Epub Nov. 14, 2005.
Letchford et al., "In Vitro Human Plasma Distribution of Nanoparticulate Paclitaxel is Dependent on the Physiochemical Properties of Poly(ethylene glycol)-block-poly(caprolactone) Nanoparticles", Eur J Pharm Biopharm, Feb. 2009:71 (2):196-206. Epub Aug. 15, 2008.
Lince et al., "Strategies to Control the Particle Size Distributio of Poly-e-caprolactone Nanoparticles for Pharmaceutical Applications", J Colloid Interface Sci, vol. 322, pp. 505-515 (2008).
Lindenberg et al., "Experimental Characterization and Multi-Scale Modeling of Mixing in Static Mixers", Chemical Engineering Science 63, pp. 4135-4149 (2008).
Liu et al., Formulating Nanoparticles by Flash Nanoprecipitation for Drug Delivery and Sustained Release, Dissertation Abstracts International, vol. 68, No. 9 (2007).
Liu et al., Mixing in a Multi-Inlet Vortex Mixer MIVM) for Flash NanoPrecipitation. 37 pages.

(56) References Cited

OTHER PUBLICATIONS

Liu et al., "Mixing in a Multi-Inlet Vortex Mixer (MIVM) for Flash NanoPrecipitation", Chemical Engineering Science, vol. 63, Issue 11, pp. 2829-2842 (Jun. 2008).
Lopedota et al., Research paper: The Use of Eudragit RS 100/cyclodextgrin Nanoparticles for The Transmucosal Administration of Glutathione, European Journal of Pharmaceutics and Biopharmaceutics vol. 72, No. 3, pp. 509-520 (2009).
Maa et al., "Effect of Primary Emulsions on Microsphere Size and Protein-Loading in the Double Emulsion Process" J. Microencapsulation, vol. 14, pp. 225-241 (1997).
Mohanraj et al., "Naoparticles—A Review" Tropical Journal of Pharmaceutical Research, vol. 5, pp. 561-573, (2006).
Nagasawa et al. "Design of a New Micromixer for Instant Mixing Based on the Collision of Micro Segments" Chem. Eng. Technol., vol. 28, No. 3, pp. 324-330, (2005).
Paul et al., eds. "Handbook of Industrial Mixing: Science and Practice", A John Wiley & Sons, Inc. Publicaiton (Nov. 2003).
Peukert et al,, "Control of Aggregation in Production and Handling of Nanoparticles" Chemical Engineering and Process, vol. 44, pp. 24-252 (2005).
Pinon-Segundo et al., "Preparation of Nanoparticles by Solvent Displacement Using a Novel Recirculation System", Pharmaceutical Development and Technology, pp. 493-501 (2006).
Rivera et al, "A Model for the Precipitation of Pentaerthritol Tetranitrate (PETN)." Ind. Eng. Chem. Process Des. Dev. vol. 17, No. 2, pp. 182-188 (1978).
Schwarzer et al. Combined Experimental/Numerical Study on the Precipitation of Nanoparticles, AIChE Journal, vol. 50, No. 12, pp, 3234-3247 (2004).
Silva et al., "A Noveal Continuous Industrial Process for Producing Hydroxyapatite Nanoparticles", Journal of Dispersion Science Technology, vol. 29, pp. 542-547 (2008).
Soppimath et al., "Biodegradable polymeric Nanoparticles as Drug Delivery Devices" Journal of Controlled Release, vol. 70, pp. 1-20 (2001).
Streiff et al., "The Design and Applicaiton of Static Mixer Technololgy", 3rd International Symposium on Mixing in Industrial Processes, Osaka, JP, pp. 107-114, (1999).
Timko et al., "Magnetite Polymer Nanospheres Loaded by Indomethacin for Anti-Inflammatory Therapy", Journal of Magentism and Magnetic Materials, May 2006;300(1):e191-e194.
Vauthier et al., "Methods for the Preparation and Manufacture of Polymeric Nanoparticles", Pharmaceutical Research, 34 pages (2008).
Wei et al., "Historical Perspectives; Biodegradable poly([var epsilon]-caprolactone)-poly(ethlene glycol) copolymers as drug delivery system" International Journal of Pharmaceutics, vol. 381, No. 1 pp. 1-18 (2009).
Xie et al., "Fabrication of PLGA Nanoparticles With a Fluidic Nanoprecipitation System", Journal of Nanobiotechnology, vol. 8, 7 pages (2010).
Zavisova et al., "Encapsulation of Indomethacin in Magnetic Biodegradable Polymer Nanoparticles", Journal of Magnetism and Magnetic Materials, Apr. 2007;311(1):379-382.
International Search Report and Written Opinion mailed May 8, 2012 for PCT/US20102/022500.

METHOD FOR FABRICATING NANOPARTICLES

RELATED APPLICATIONS

This is a continuation application of application Ser. No. 13/357,977 filed Jan. 25, 2012, which claims priority from U.S. Provisional Application No. 61/437,142 filed on Jan. 28, 2011. The contents of both these prior application specifications are incorporated herein by reference.

BACKGROUND

The present invention relates generally to methods and systems for fabricating nanoparticles, and more particularly, it relates to such methods and systems that allow concurrent generation of a nanoparticle-containing fluid and its filtration to increase the concentration of the nanoparticles therein.

A variety of methods and systems are known for generating nanoparticles. In many such methods, a batch of nanoparticles is initially generated as a suspension, and subsequently the suspension is subjected to various stages of filtration. For example, in one such method, a polymer-containing organic phase is mixed with an aqueous phase to generate a primary emulsion, which is turned into a fine emulsion, e.g., by employing a high-pressure homogenizer. The fine emulsion is quenched, e.g., via its introduction into a quench tank of deionized water, to form a suspension of nanoparticles. Once the formation of the nanoparticles is completed, the nanoparticle suspension is subjected to multiple filtration stages, such as concentration, and diafiltration, to isolate the nanoparticles.

Such conventional methods for fabricating and isolating nanoparticles can be time consuming. Further, many conventional systems for generating nanoparticles require a large space for the processing components, especially as the nanoparticle production process is scaled up.

Thus, there is a need for improved methods and systems of fabricating and isolating nanoparticles that would provide reduced processing time as well as a smaller system footprint.

SUMMARY

In one aspect, the present invention provides a method of filtering a fluid containing nanoparticles, which comprises the steps of introducing a stream of the nanoparticle-containing fluid into one or more holding vessels, and extracting at least a part of a nanoparticle-containing fluid accumulated in the holding vessel. The extracted nanoparticle-containing fluid is passed through a filtration module to separate a nanoparticle-containing retentate from a permeate, and the retentate is returned to the same or a different holding vessel.

In a related aspect, the above method is scalable to allow filtering a wide range of volumes of the fluid containing nanoparticles.

The permeate is drained from the filtration module. In some embodiments, the drainage rate of the permeate out of the filtration module is, or selected to be, substantially equal to the flow rate of the nanoparticle-containing fluid stream into the holding vessel. In other embodiments, the drainage rate of the permeate out of the filtration module can be less than or greater than the flow rate of the nanoparticle-containing fluid stream into the holding vessel. In an embodiment, the drainage rate out of the holding vessel is adjustable and the method includes drainage at a first and a second rate. In an embodiment, the drainage rate out of the filtration module is adjustable and the method includes drainage at a first and a second rate.

In some embodiments, each pass of the nanoparticle-containing fluid through the filtration module results in a retentate having a concentration of the nanoparticles that is higher by about 5 to about 15 percent (e.g., about 10 percent) than the concentration of the nanoparticles in the fluid entering the filtration module. In an embodiment, a pass has a predetermined volume, e.g., a volume at about 5-100%, or about 10-90%, or about 15-80%, or about 20-70%, or about 30-50% of the volume of the fluid in the holding vessel.

In some embodiments, the volume of the fluid passing through the filtration module during a production run, which can include one or, more typically, multiple filtration cycles, can be predetermined, e.g., a volume at about 5-500%, about 10-250%, about 15-200%, about 20-100%, or about 30-50% of the volume of a component used in the method, e.g., the holding vessel, or the total volume of the system, or about 5-500%, 10-250%, 15-200%, of 30-50% of the volume of the nanoparticle-containing fluid that enters the holding vessel in a production run.

In some embodiments, the above process can yield at least about 10 grams of the nanoparticles in the holding vessel. For example, the above process can yield about 10 grams to about 100 kilograms of the nanoparticles, e.g., about 10 grams to about 50 kilograms, or about 10 grams to about 20 kilograms, or about 10 grams to about 10 kilograms, or about 10 grams to about 1 kilogram, or about 10 grams to about 500 grams, or about 10 grams to about 400 grams, or about 10 grams to about 300 grams, or about 10 grams to about 200 grams, or about 10 grams to about 100 grams, or about 10 grams to about 50 grams, or about 10 grams to about 20 grams, of the nanoparticles in the holding vessel. In some embodiments, the above process can yield the nanoparticles at a rate of at least about 2.5 grams/hour (e.g., in a range of about 3 to about 5 grams/hour). For example, in some embodiments, the above process can yield the nanoparticles at a rate of about 2.5 grams/hour to about 100 grams/hour, or about 2.5 grams/hour to about 50 grams/hour, or about 2.5 grams/hour to about 25 grams/hour, or about 2.5 grams/hour to about 10 grams/hour.

In some embodiments, the volume of the holding vessel is equal to or less than about 10 liters, e.g., in a range of about 1 liter to about 5 liters, though in other embodiments the holding vessel can have a greater volume. In some embodiments, the above process yields about 10 grams to about 1 kilogram of the nanoparticles, e.g., about 10 grams to about 500 grams, or about 10 grams to about 400 grams, or about 10 grams to about 300 grams, or about 10 grams to about 200 grams, or about 10 grams to about 100 grams, or about 10 grams to about 50 grams of the nanoparticles, in a holding vessel having a volume less than about 10 liters, e.g., a volume in a range of about 1 liter to about 10 liters, e.g., about 1 liter to about 5 liters, or about 2 liters to about 5 liters. In some embodiments, the above process can yield at least about 10 grams of nanoparticles by employing a holding vessel whose volume is equal to or less than about 1 liter.

A variety of flow rates can be selected for the flow of the nanoparticle-containing fluid into the holding vessel, e.g., based on the characteristics of a device utilized for generating the nanoparticles, the scale of nanoparticle production, the types of nanoparticles generated, etc. In some cases, the volume of permeate that is drained out of the filtration module during a single pass of the nanoparticle-containing fluid through the filtration module can be in a range of about 5 percent to about 15 percent (e.g., about 10 percent) of the volume of the nanoparticle-containing fluid that enters the filtration module.

The filtration cycle can be repeated until the fluid contained in the holding vessel has a desired concentration of the nanoparticles. Once a desired concentration of the nanoparticles is achieved, the fluid contained in the holding vessel, or at least a portion thereof, can be collected, or the fluid can be subjected to further filtration steps, as discussed in more detail below. Further, in some cases, a portion of the nanoparticle-containing retentate can be drained from the system as filtration is performed, for example, for monitoring. In some embodiments, the filtration cycle is terminated when the concentration of the nanoparticles in the holding vessel is at least about 10 grams/liter.

In an embodiment, the cycle is repeated until the resulting product, e.g. in the holding vessel, has reached a preselected amount of nanoparticles, e.g., about 100 kilograms, or about 50 kilograms, or about 20 kilograms, or about 10 kilograms, or about 5 kilograms, or about 1 kilogram, or about 500 grams, or about 400 grams, or about 300 grams, or about 200 grams, or about 100 grams, or about 50 grams, or about 20 grams, or about 10 grams, and/or has reached a preselected concentration, e.g., about 10 kilograms/liter, or about 1 kilogram/liter, or about 500 grams/liter, or about 400 grams/liter, or about 300 grams/liter, or about 200 grams/liter, or about 100 grams/liter, or about 50 grams/liter, or about 40 grams/liter, or about 30 grams/liter, or about 20 grams/liter, or about 10 grams/liter, or about 5 grams/liter or about 1 gram/liter, after the passage of a volume of the nanoparticle-containing fluid through the filtration module of between about 2-500, or about 5-100, or about 10-50 times the volume of the fluid-containing nanoparticles that entered the holding vessel.

In some embodiments, the step of introducing the nanoparticle-containing fluid stream into the holding vessel comprises establishing a flow, e.g., a continuous flowing stream, of the fluid into the holding vessel. In some other embodiments, the step of introducing the nanoparticle-containing fluid into the holding vessel comprises establishing an intermittent flow of the fluid into the holding vessel.

In a related aspect, the step of extracting the nanoparticle-containing fluid from the holding vessel is performed concurrently with the step of introducing the nanoparticle-containing fluid stream into the holding vessel. In some embodiments, the introduction of the nanoparticle-containing fluid stream into the holding vessel can have a temporal overlap with the extraction of at least a portion of the nanoparticle-containing fluid from the holding vessel for passage through the filtration module. In some embodiments, the extraction of the nanoparticle-containing fluid from the holding vessel begins after the introduction of the nanoparticle-containing fluid stream into the holding vessel but before the completion of the flow of the nanoparticle-containing fluid into the holding vessel. In some embodiments, the introduction of the nanoparticle-containing fluid stream into the holding vessel can begin and continue for some time before the extraction of at least a portion of the nanoparticle-containing fluid from the holding vessel is started. In one implementation of such an embodiment, the extraction of the nanoparticle-containing fluid from the holding vessel can continue for some time after the introduction of the nano-particle containing fluid stream into the holding vessel is terminated. Alternatively, the introduction of the nanoparticle-containing fluid into the holding vessel can continue for some time after the extraction of the nanoparticle-containing fluid from the holding vessel is terminated. Further, in some embodiments, the introduction of the nanoparticle-containing fluid into the holding vessel and the extraction of the nanoparticle-containing fluid from the holding vessel are terminated at the same time.

A variety of filtration modules can be employed in the above filtration method. In some embodiments, the filtration module provides tangential flow filtration (TFF). In some cases, each pass of the nanoparticle-containing fluid through the TFF filtration module results in a retentate having an increase in a range of about 5 percent to about 15 percent (e.g., about 10 percent) in the concentration of the nanoparticles.

In some embodiments, the nanoparticle-containing fluid comprises a stream of an aqueous solution in which the nanoparticles are entrained. In some cases, the aqueous solution can further include one or more organic solvent(s). Some examples of such organic solvent(s) include, without limitation, acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO).

In some embodiments, the nanoparticle-containing fluid comprises a colloid stabilizer. Some examples of colloid stabilizers include, without limitation, poly(vinyl alcohol), Dextran and pluronic F68, poly (vinyl pyrrolidone), solutol, Tween 80, poloxamer, carbopol, poly-ethylene glycol, sodium dodecyl sulfate, poly ($\epsilon$-caprolactone), peptides, and carbohydrates. In some cases, the filtration module can remove at least a portion of the colloid stabilizer from the nanoparticle-containing fluid as it passes through the module.

In a related aspect, in the above method, subsequent to obtaining a desired concentration of the nanoparticles in the holding vessel, the product, e.g., fluid contained in the holding vessel, can be subjected to another filtration process, such as a diafiltration process, to remove, e.g., at least a portion of organic solvent(s), colloid stabilizers and other additives present in the nanoparticle-containing fluid. For example, a subsequent diafiltration process can be performed by passing the fluid from the holding vessel through a filtration module (e.g., the same filtration module used during the first filtration stage discussed above or a different filtration module) to separate a portion of the fluid that contains the above impurities but is substantially free of the nanoparticles (permeate) from a nanoparticle-containing portion of the fluid (retentate). The nanoparticle-containing retentate is returned to the holding vessel while a replacement fluid (e.g., deionized water) is added to the vessel. The permeate is drained from the filtration module. In many cases, the volume of the replacement fluid added to the holding vessel is equal to the volume of the removed permeate. For example, in some cases, the rate at which the permeate is drained from the filtration module is substantially equal to the rate at which the replacement fluid is added to the holding vessel. Alternatively, in other cases, the rate at which the permeate is drained from the filtration module during the diafiltration process can be less or greater than the rate at which the replacement fluid is added to the holding vessel. The filtration cycle can be repeated until the concentration of the impurities is reduced to a desired level.

In another aspect, a system for filtering a fluid containing nanoparticles is disclosed, which comprises a holding vessel adapted to receive a stream of the nanoparticle-containing fluid, a filtration module fluidly connected to the vessel to receive at least a portion of a nanoparticle-containing fluid accumulated in the holding vessel to separate a nanoparticle-containing retentate from a permeate, and a return path providing a fluid passage for the nanoparticle-containing retentate back to the holding vessel. In some embodiments, the filtration module can provide tangential flow filtration (TFF).

In a related aspect, the holding vessel is adapted for fluid coupling to a device for generating nanoparticles contained in a fluid. By way of example, an input port of the holding vessel can be in fluid communication with an output port of the nanoparticle-generating device, e.g., via a conduit, to receive a stream of the nanoparticle-containing fluid from the device. In some implementations, a pump disposed between the nanoparticle-generating device and the holding vessel facilitates the transfer of the nanoparticle-containing fluid from the device to the holding vessel. In some embodiments, the holding vessel is configured to have concurrent fluid couplings with the nanoparticle-generating device and the filtration module. This allows a stream of the nanoparticle-containing fluid to be introduced into the holding vessel while a portion of the fluid accumulated in the holding vessel is extracted via an output port thereof to be passed through the filtration module.

In the above system, the filtration module can include a drainage port for draining the permeate from the module. In some embodiments, a pump coupled to this drainage port can facilitate the removal of the permeate. In some cases, the pump is configured to remove the permeate from the filtration module at a rate that is substantially equal to a rate at which the holding vessel receives the nanoparticle-containing fluid.

The system can further include an output port fluidly coupled to the holding vessel for draining the fluid contained in that vessel. In some implementations, the system can include an output port fluidly coupled to the return path to allow removing a portion of the retentate exiting the filtration module, e.g., for testing or monitoring of the retentate and/or collection of the nanoparticles.

In some embodiments, the system can further include a reservoir for containing a replacement fluid (e.g., deionized water). The reservoir is in fluid coupling with the vessel to provide a flow of the replacement fluid thereto, e.g., during a diafiltration process.

In another aspect, a system for generating nanoparticles is disclosed, which comprises a device for generating a plurality of nanoparticles contained in a fluid stream, a holding vessel in fluid communication with the device to receive the nanoparticle-containing fluid stream, and a filtration module (e.g., a TFF module) in fluid communication with the holding vessel to receive at least a portion of a nanoparticle-containing fluid accumulated in the vessel to separate a nanoparticle-containing retentate from a permeate. The system further includes a return path providing a fluid passage for the nanoparticle-containing retentate back to the holding vessel.

The filtration module can include a drainage port for removing the permeate therefrom. In some implementations, a pump is coupled to the drainage port to facilitate the removal of the permeate from the filtration module. The pumping rate for removing the permeate from the filtration module can be adjusted to be substantially equal to the rate at which the nanoparticle-containing fluid stream enters the holding vessel. Alternatively, the pumping rate for removing the permeate from the filtration module can be greater or less than the rate at which the nanoparticle-containing fluid stream enters the holding vessel, e.g., based on the stage of processing.

In some embodiments, the nanoparticle-generating device is adapted to generate polymeric nanoparticles by introducing a polymer solution into a mixed flowing stream of an anti-solvent to cause controlled precipitation of polymeric nanoparticles. In some implementations, the device can include a conduit having a first input port for receiving an anti-solvent, e.g., from a reservoir in which the anti-solvent is stored, and at least one static mixer disposed in the conduit to generate a mixed flowing stream of the anti-solvent, where the static mixer extends from a proximal end to a distal end. The conduit has a second input port disposed relative to the static mixer so as to allow introducing a polymer solution, e.g., from a reservoir in which the polymer solution is stored, into the mixed flowing stream of the anti-solvent to generate polymeric nanoparticles, e.g., via precipitation. In some implementations, the volume of the holding vessel is at least about 10 times less than the combined volumes of the reservoirs in which the anti-solvent and the polymer solution are stored.

In another aspect, a system for filtering a fluid containing nanoparticles is disclosed, which comprises a holding vessel that contains a nanoparticle-containing fluid and is adapted to receive a stream of the nanoparticle-containing fluid. The system further includes a filtration module fluidly connected to the vessel to receive at least a portion of a nanoparticle-containing fluid accumulated in the holding vessel to separate a nanoparticle-containing retentate from a permeate, and a return path providing a fluid passage for the nanoparticle-containing retentate back to the holding vessel. In some embodiments, the filtration module can provide tangential flow filtration (TFF).

In another aspect, the invention discloses a preparation of polymeric nanoparticles produced by a method described herein, e.g., by introducing a stream of a nanoparticle-containing fluid into a holding vessel, extracting at least a part of a nanoparticle-containing fluid accumulated in the holding vessel, passing the extracted nanoparticle-containing fluid through a filtration module to separate a nanoparticle-containing retentate from a permeate, and returning the retentate to the vessel. The filtration cycle can be repeated until a desired concentration of the nanoparticles in the holding vessel is achieved.

In some embodiments, the above preparation of polymeric nanoparticle includes at least about 100 grams, or about 200 grams, or about 500 grams, or about 1000 grams, or about 2000 grams, or about 10,000 grams, or about 100,000 grams of the nanoparticles. In some embodiments, the preparation includes a concentration of at least about 10 grams/liter of the nanoparticles. For example, in some embodiments, the preparation includes a concentration of at least about 10 kilograms/liter, or about 1 kilogram/liter, or about 500 grams/liter, or about 400 grams/liter, or about 300 grams/liter, or about 200 grams/liter, or about 100 grams/liter, or about 50 grams/liter, or about 40 grams/liter, or about 30 grams/liter, or about 20 grams/liter, or about 10 grams/liter, or about 5 grams/liter or about 1 gram/liter of the nanoparticles.

In a related aspect, the above preparation of polymeric nanoparticles includes poly(lactic-co-glycolic acid) (PLGA) as at least one polymeric component. In some embodiments, the PLGA polymer is attached to a therapeutic agent. For example, the therapeutic agent can be an anti-neoplastic agent. In some embodiments, the anti-neoplastic agent is a taxane (e.g., paclitaxel, docetaxel, larotaxel, or cabazitaxel).

In an embodiment, the preparation is a pharmaceutically acceptable preparation, and includes, e.g., a pharmaceutically acceptable excipient, e.g., a lyoprotectant. In an embodiment, the pharmaceutically acceptable preparation is a liquid or a lyophilized powder.

In an embodiment, a method described herein further includes dividing a first pharmaceutically acceptable preparation made by a method described herein into smaller aliquots and optionally packaging a plurality of aliquots into gas and/or liquid-tight containers.

In an embodiment, a method described herein further includes testing said product (e.g., the preparation of the nanoparticles) to determine if it meets a preselected reference value, e.g., a value for concentration, particle size, purity, polydispersity index, or other particle properties described herein.

In an embodiment, the above preparation of the nanoparticles is produced by a single or multiple production runs.

Further understanding of the invention can be obtained by reference to the following detailed description in conjunction with the associated drawings, which are described briefly below. Like numerals refer to like parts throughout the specification.

DETAILED DESCRIPTION

Figure 1:
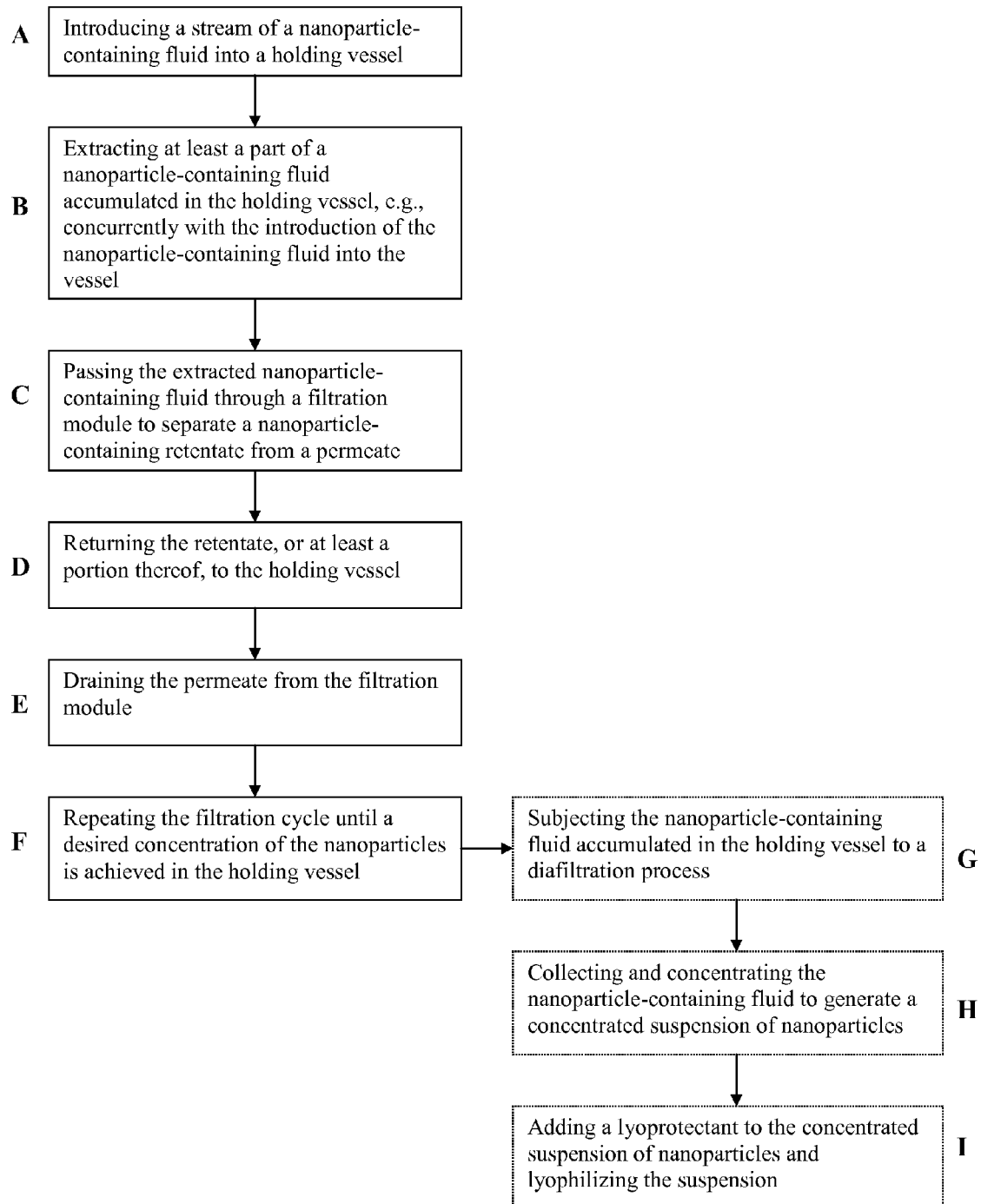
FIG. 1 is a flow chart depicting various steps in an embodiment of a method according to the teachings of the invention for filtering a nanoparticle-containing fluid, FIG. 2 schematically depicts a system according to an embodiment of the invention for generating nanoparticles, FIG. 3 schematically depicts a system according to another embodiment of the invention for generating nanoparticles, and FIG. 4 schematically depicts a system according to another embodiment of the invention for generating nanoparticles by employing a nanoprecipitation process.

The present invention relates generally to methods and systems for generating nanoparticles, e.g., polymeric nanoparticles, and in particular, to methods and systems for filtering a nanoparticle-containing fluid to isolate the nanoparticles. As discussed in more detail below, in many embodiments the filtration of a nanoparticle-containing fluid is performed concurrently with its generation.

The following definitions are provided for a variety of terms and phrases utilized herein:

Nanoparticle:

The term "nanoparticle" is used herein to refer to a material structure whose size in any dimension (e.g., x, y, and z Cartesian dimensions) is less than about 1 micrometer (micron), e.g., less than about 500 nm or less than about 200 nm or less than about 100 nm, and greater than about 5 nm. A nanoparticle can have a variety of geometrical shapes, e.g., spherical, ellipsoidal, etc. The term "nanoparticles" is used as the plural of the term "nanoparticle."

Filtration:

The term "filtration" is used herein consistent with its common meaning in the art to refer to a process by which a feed material is partitioned into at least two components, where typically at least one of those components is retained and the other component(s) is discarded. In some cases, such partitioning of the feed material is achieved by passing the feed material over or through a porous or a semipermeable barrier (e.g., a porous or a semipermeable membrane).

Retentate:

The term "retentate" is used herein consistent with its common meaning in the art to refer to at least one component of a feed material (e.g., a portion of a feed fluid) that is separated from the rest of the feed material via filtration and is retained, e.g., for use or further processing.

Permeate:

The term "permeate" is used herein interchangeably with the term "filtrate" and consistent with its common meaning in the art to refer to at least one component of a feed material (e.g., a portion of a feed fluid) that is separated from the retentate, e.g., by passing through a porous or a semipermeable barrier (e.g., a porous or a semipermeable membrane). The permeate is typically discarded.

Static Mixer:

The term "static mixer" or "motionless mixer" as used herein refers to a device that includes one or more substantially stationary mixing elements, e.g., baffles such as blades, plates, vanes, that are adapted for placement in the path of a flowing fluid, e.g., a fluid flowing through a conduit, to produce a pattern of flow divisions and splits to accomplish mixing, e.g., radial mixing via radial circulation or exchange, in the flowing fluid. Although the stationary mixing elements are typically immovable within the conduit, some limited movement of the stationary elements relative to the conduit can occur so long as such limited movement does not contribute substantially to the mixing of the flowing fluid. In a static mixer having multiple stationary elements, these elements are typically arranged in series and in a staggered orientation relative to one another.

Mixed Flowing Stream:

The term "mixed flowing stream" as used herein refers to a flowing stream of a fluid, e.g., a liquid, that exhibits active motion normal to its direction of flow.

Polymer Solution:

The term "polymer solution" as used herein refers to a solution comprising one or more polymers dissolved in a liquid solvent, which is herein also referred to as process solvent. The polymer(s) are typically sufficiently soluble in the solvent such that a concentration of at least about 0.1 percent by weight, and preferably at least about 0.2 percent by weight (e.g., 1 percent by weight), of the polymer(s) can be dissolved in the solvent at room temperature. The polymer solution can also include a variety of additives, such as therapeutic and/or imaging agents or other supplemental additives useful for the production and/or subsequent use of the nanoparticles.

Anti-Solvent:

The term "anti-solvent" as used herein refers to a liquid, or a mixture of liquids, which is incapable of dissolving any appreciable concentration (e.g., a concentration equal to or greater than about 0.1% at room temperature) of the polymer(s) of the polymer solution, but is miscible, or at least partially miscible, with the process solvent. In some embodiments, the anti-solvent and the process solvent can be mixed in all proportions to form a homogeneous solution. When combined with the polymer solution, the anti-solvent causes at least a portion of the polymer to precipitate.

Colloid Stabilizer:

The term colloid stabilizer as used herein refers to an additive added to the anti-solvent and/or the polymer solution to prevent or retard an unwanted alteration of the physical state of the particles, e.g., a colloid stabilizer can inhibit aggregation of the nanoparticles. For example, a colloid stabilizer can inhibit aggregation of the nanoparticles during and/or after their formation.

Average Particle Size:

The term "average particle size" is a length dimension which is designated herein as Z average or $Z_{ave}$, and as used herein refers to the intensity weighted mean hydrodynamic size of an ensemble collection of particles measured by dynamic light scattering (DLS). The Z average is derived from a Cumulants analysis of a measured autocorrelation curve, wherein a single particle size is assumed and a single exponential fit is applied to the autocorrelation function. The autocorrelation function ($G(\tau)$) is defined as follows:

$$G(\tau) = \langle I(t) \cdot I(t+\tau) \rangle = A[1+B\exp(-2\Gamma\tau)] \qquad \text{Eq. (3)}$$

wherein, $$\Gamma = Dq^2 \qquad \text{Eq. (4)}$$

$$q = \frac{4\pi \tilde{n}}{\lambda_0} \sin\left(\frac{\theta}{2}\right) \qquad \text{Eq. (5)}$$

$$D = \frac{kT}{6\pi\mu R_H}, \qquad \text{Eq. (6)}$$

wherein,

I represents the light scattering intensity,
t represents an initial time,
τ represents the delay time,
A represents an amplitude (or intercept) of the autocorrelation function,
B represents the baseline,
D represents the diffusion coefficient,
q represents the scattering vector,
k represents the Boltzmann constant,
$\lambda_0$ represents the vacuum wavelength of a laser source employed for the light scattering measurements,
ñ represents the index of refraction of the medium,
θ represents the scattering angle,
T represents the absolute temperature (Kelvin),
μ represents the viscosity of the medium, and
$R_H$ represents the hydrodynamic radius.

In the Cumulants analysis, the exponential fitting expression of Eq. (3) is expanded as indicated below as expression γ(τ) in Eq. (7) to account for polydispersity, which is defined in more detail below, or peak broadening, $$\begin{aligned} y(\tau) &= \frac{1}{2}\ln[G(\tau) - A] \\ &= \frac{1}{2}\ln[AB\exp(-2\Gamma\tau + \mu_2\tau^2)] \\ &\cong \frac{1}{2}\ln[AB] - \langle\Gamma\rangle\tau + \frac{\mu_2}{2}\tau^2 \\ &= a_0 - a_1\tau + a_2\tau^2 \end{aligned} \qquad \text{Eq. (7)}$$

wherein $\mu_2$ is a fitting parameter and the other parameters are defined above.

The dynamic light scattering data can be fit to the above expression (Eq. (7)) to obtain values of the parameters $\alpha_0$, $\alpha_1$, and $\alpha_2$. The first Cumulant moment ($\alpha_1$) can be utilized to obtain $Z_{ave}$ as follows:

$$Z_{ave} = \frac{1}{a_1} \frac{kT}{3\pi\mu} \left[\frac{4\pi\tilde{n}}{\lambda_0}\sin\left(\frac{\theta}{2}\right)\right]^2 \qquad \text{Eq. (8)}$$

wherein the parameters are defined above.

The first Cumulant moment ($\alpha_1$) and the second Cumulant moment ($\alpha_2$) can be used to calculate another parameter known as polydispersity index (PdI), which is discussed in more detail below, as follows:

$$PdI = \frac{2a_2}{a_1^2} \qquad \text{Eq. (9)}$$

Polydispersity Index:

The term "polydispersity index" is used herein as a measure of the size distribution of an ensemble of particles, e.g., nanoparticles. The polydispersity index is calculated as indicated in the above Eq. (9) based on dynamic light scattering measurements.

Particle Size Distribution:

If it is assumed that an ensemble of particles exhibit a Gaussian size distribution, then the particle size distribution of such an ensemble is a length dimension that can be defined as the square root of the standard deviation of the Gaussian distribution ($\sigma^2$) as follows:

$$\sigma^2 = PdI \cdot Z_{ave}^2 \qquad \text{Eq. (10)}$$

$$\text{Particle Size Distribution} = \sqrt{\sigma^2} \qquad \text{Eq. (11)}$$

wherein $Z_{ave}$ is defined by Eq. (8) above.

With reference to flow chart of FIG. 1, in an exemplary embodiment of a method according to the teachings of the invention for filtering a nanoparticle-containing fluid, a stream of the fluid can be introduced into a holding vessel (step A). At least a part of a nanoparticle-containing fluid accumulated in the holding vessel can be extracted (step B) and passed through a filtration module to separate a nanoparticle-containing retentate from a permeate (step C). The retentate, or at least a portion thereof, can be returned to the holding vessel (step D). Further, the permeate generated as the nanoparticle-containing fluid passes through the filter can be drained from the filtration module (step E).

The return of the retentate back to the holding vessel establishes a loop, e.g., a closed-loop, filtration cycle. The filtration cycle can be repeated until a desired concentration of the nanoparticles is achieved in the holding vessel (step F). In some implementations, a portion of the retentate can be collected upon exiting the filtration module, e.g., via a port coupled to a fluid return path connecting an output port of the filtration module to the holding vessel, for testing and monitoring and/or collecting the nanoparticles.

In the above method, the flow of the nanoparticle-containing fluid into the holding vessel can be a continuous flow, or alternatively, an intermittent flow. Similarly, the flow of the nanoparticle-containing fluid extracted from the holding vessel to the filtration module can be implemented as a continuous or an intermittent flow.

In some embodiments, a stream of the particle-containing fluid is introduced into the holding vessel (e.g., via an input port thereof) concurrently with extracting at least a part of a nanoparticle-containing fluid accumulated in the holding vessel (e.g., via an output port thereof) to be filtered by the filtration module. In some implementations of such an embodiment, the rate of flow of the nanoparticle-containing fluid into the holding vessel and the drainage rate of the permeate out of the filtration module are selected to be substantially equal in order to ensure that a steady state fluid volume is maintained in the holding vessel. A variety of flow rates can be employed. By way of example, the flow rate of the nanoparticle-containing fluid into the holding vessel can be in a range of about 20 ml/min to about 2000 ml/min. As discussed in more detail below, in some embodiments, in a subsequent diafiltration step, the drainage rate of the permeate out of the filtration module can be equal to, less than or greater than the rate at which a replacement fluid is introduced into the holding vessel.

A variety of filtration modules can be employed in the above method for filtering a nanoparticle-containing fluid. By way of example, the filtration module can be a tangential flow filtration (TFF) system. By way of example, in such a TFF system, the nanoparticle-containing fluid can flow tangentially over a porous membrane with a pore size suitable for retaining the nanoparticles as a retentate, while allowing at least a portion of the other constituents of the fluid (e.g., water, organic solvent(s), PVA stabilizer) to pass through as a permeate (filtrate).

In some embodiments, the nanoparticle-containing fluid stream that is introduced into the holding vessel can comprise an aqueous solution in which the nanoparticles are entrained. In some cases, the aqueous solution further includes one or more organic solvents. By way of example, the organic solvent can comprise any of acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO). The filtration module can remove at least a portion of the liquid (e.g., water and/or organic solvent(s)) as the nanoparticle-containing fluid passes through the filtration module to generate a retentate having a greater concentration of the nanoparticles as it exits the filtration module.

In some embodiments, the nanoparticle-containing fluid stream that is introduced into the holding vessel can comprise a colloid stabilizer. In such embodiments, the filtration module removes at least a portion of the colloid stabilizer as the nanoparticle-containing fluid passes through it. By way of example, the colloid stabilizer can be any of poly(vinyl alcohol), Dextran and pluronic F68, poly (vinyl pyrrolidone), solutol, Tween 80, poloxamer, carbopol, poly-ethylene glycol, sodium dodecyl sulfate, poly (ε-caprolactone), peptides, and carbohydrates.

With continued reference to the flow chart of FIG. 1, once a desired concentration of the nanoparticles is achieved in the holding vessel, the nanoparticle-containing fluid accumulated in the vessel can be subjected to a diafiltration process (step G), e.g., to further remove organic solvent(s) and colloid stabilizer (e.g., PVA), if any, present in the fluid. The diafiltration can be achieved, for example, by introducing a replacement fluid (e.g., deionized water) from a reservoir into the holding vessel as the fluid accumulated in the holding vessel is passed through a filtration module (e.g., a TFF system) to separate a nanoparticle-containing retentate from a permeate (filtrate).

Subsequent to the completion of the diafiltration process, the aqueous nanoparticle-containing fluid accumulated in the holding vessel can be collected and concentrated (step H), e.g., via filtration, to generate a concentrated suspension of the nanoparticles. In some embodiments, a compound for protecting the nanoparticles in a subsequent lyophilization step, e.g., a lyoprotectant and/or a cryoprotectant, can be added to the suspension followed by lyophilizing the suspension (step I). The protective compound, e.g., the lyoprotectant and/or the cryoprotectant, can be added prior to or after the step of concentrating the suspension, to protect the nanoparticles in a subsequent lyophilization step. By way of example, the lyoprotectant can be, without limitation, a derivatized cyclic oligosaccharide, e.g., a derivatized cyclodextrin, e.g., 2 hydroxy propyl-β cyclodextrin, e.g., partially etherified cyclodextrins (e.g., partially etherified β cyclodextrins) disclosed in U.S. Pat. No. 6,407,079, the contents of which are incorporated herein by this reference. In an embodiment, the lyoprotectant is a disaccharide. The term "disaccharide," as used herein refers to a compound or a chemical moiety formed by 2 monosaccharide units that are bonded together through a glycosidic linkage, for example through 1-4 linkages or 1-6 linkages. A disaccharide may be hydrolyzed into two monosaccharides. Exemplary disaccharide lyoprotectants include sucrose, trehalose, lactose, maltose and the like.

As noted above, in some embodiments, polymeric nanoparticles can be formed via precipitation, typically over a short time period, upon contact of a polymer solution with a mixed flowing stream of an anti-solvent. The polymer solution can comprise a polymer dissolved in a process solvent, wherein the process solvent is miscible, or at least partially miscible, with the anti-solvent. Further, in some embodiments, the polymer solution can include one or more additives, such as a variety of therapeutic and imaging agents. The polymer solution (and in some implementations a polymer dispersion or mixed polymer solution/dispersion) can be introduced into a mixed flowing stream of an anti-solvent such that precipitation of polymeric nanoparticles occurs. The nanoparticles are carried by a flowing stream comprising a mixture of the anti-solvent and the process solution (and in many cases predominantly the anti-solvent) into the holding vessel.

A variety of polymers, process solvents, and anti-solvents can be employed in the precipitation process to form nanoparticles. By way of example, the polymers can include the following monomers (or sub-units): acrylates, acrylonitriles such as methacrylnitrile, vinyls, aminoalkyls, styrenes, and lactic acids. Some examples of acrylates include, without limitation, methyl acrylate, ethyl acrylate, propyl acrylate, n-butyl acrylate, isobutyl acrylate, 2-ethyl acrylate, and t-butyl acrylate. Some examples of vinyls include, without limitation, vinyl acetate, vinylversatate, vinylpropionate, vinylformamide, vinylacetamide, vinylpyridines and vinylimidazole. Some examples of aminoalkyls include, without limitation, aminoalkylacrylates, amino alkyl-methacrylates and amino alkyl(meth)acrylamides.

In some embodiments, the polymer can be an amphiphilic copolymer that is formed of monomers exhibiting different hydrophilic and hydrophobic properties. For example, in some embodiments, the polymer has a hydrophilic portion and a hydrophobic portion. In some embodiments, the polymer is a block copolymer. In some embodiments, the amphiphilic copolymer is formed of blocks (groups) of monomers or sub-units, where some blocks are substantially hydrophobic while other blocks are substantially hydrophilic. For example, in diblock copolymers the blocks are arranged as a series of two blocks having similar hydrophobic or hydrophilic properties while in triblock copolymers, the blocks are arranged as a series of three blocks having similar hydrophobic or hydrophilic properties. In some embodiments, the amphiphilic polymer comprises two regions, one of which is hydrophilic and the other hydrophobic, where the two regions together comprise at least about 70% by weight of the polymer (e.g., at least about 80%, at least about 90%, at least about 95%).

In some embodiments, the hydrophobic portion of the polymer is a biodegradable polymer (e.g., PLA, PGA, PLGA, PCL, PDO, polyanhydrides, polyorthoesters, or chitosan). In some embodiments, the hydrophobic portion of the polymer is PLA. In some embodiments, the hydrophobic portion of the polymer is PGA. In some embodiments, the hydrophobic portion of the polymer is a copolymer of lactic and glycolic acid (e.g., PLGA).

In some embodiments, the hydrophilic portion of the polymer is polyethylene glycol (PEG). In some embodiments, the hydrophilic portion of the polymer has a molecular weight of from about 1 kDa to about 20 kDa (e.g., from about 1 kDa to about 15 kDa, from about 2 kDa to about 12 kDa, from about 6 kDa to about 20 kDa, from about 5 kDa to about 10 kDa, from about 7 kDa to about 10 kDa, from about 5 kDa to about 7 kDa, from about 6 kDa to about 8 kDa, about 6 kDa, about 7 kDa, about 8 kDa, or about 9 kDa). In some embodiments, the ratio of molecular weight of the hydrophilic to hydrophobic portions of the polymer is from about 1:20 to about 1:1 (e.g., about 1:10 to about 1:1, about 1:2 to about 1:1, or about 1:6 to about 1:3).

In some embodiments, the hydrophilic portion of the polymer terminates in a hydroxyl moiety prior to conjugation to an agent. In some embodiments, the hydrophilic portion of the polymer terminates in an alkoxy moiety. In some embodiments, the hydrophilic portion of the polymer is a methoxy PEG (e.g., a terminal methoxy PEG).

In some embodiments, the hydrophilic portion of the polymer is attached to the hydrophobic portion through a covalent bond. In some embodiments, the hydrophilic polymer is attached to the hydrophobic polymer through an amide, ester, ether, amino, carbamate, or carbonate bond (e.g., an ester or an amide).

In some embodiments, the polymer is a biodegradable polymer (e.g., polylactic acid (PLA), polyglycolic acid (PGA), poly(lactic-co-glycolic acid) (PLGA), polycaprolactone (PCL), polydioxanone (PDO), polyanhydrides, polyorthoesters, or chitosan). In some embodiments, the polymer is a hydrophobic polymer. In some embodiments, the polymer is PLA. In some embodiments, the polymer is PGA.

In some embodiments, the polymer is a copolymer of lactic and glycolic acid (poly(lactic-co-glycolic acid) (PLGA)). In some embodiments, the polymer is a PLGA-ester. In some embodiments, the polymer is a PLGA-lauryl ester. In some embodiments, the polymer comprises a terminal free acid prior to conjugation to an agent. In some embodiments, the polymer comprises a terminal acyl group (e.g., an acetyl group). In some embodiments, the ratio of lactic acid monomers to glycolic acid monomers is from about 0.1:99.9 to about 99.9:0.1. In some embodiments, the ratio of lactic acid monomers to glycolic acid monomers is from about 75:25 to about 25:75 (e.g., about 50:50 or about 75:25).

In some embodiments, the average molecular weight of the polymer is from about 1 kDa to about 20 kDa (e.g., from about 1 kDa to about 15 kDa, from about 2 kDa to about 12 kDa, from about 6 kDa to about 20 kDa, from about 5 kDa to about 10 kDa, from about 7 kDa to about 10 kDa, from about 5 kDa to about 7 kDa, from about 6 kDa to about 8 kDa, about 6 kDa, about 7 kDa, about 8 kDa, or about 9 kDa). In some embodiments, the polymer has a glass transition temperature of about 20° C. to about 60° C. In some embodiments, the polymer has a polymer polydispersity index equal to or less than about 2.5 (e.g., less than or equal to about 2.2, or less than or equal to about 2.0).

By way of further illustration, some examples of suitable polymers include poly(lactide-co-glycolide), poly(lactide), poly(epsilon-caprolactone), poly(isobutylcyanoacrylate), poly(isohexylcyanoacrylate), poly(n-butylcyanoacrylate), poly(acrylate), poly(methacrylate), poly(lactide)-poly(ethylene glycol), poly(lactide-co-glycolide)-poly(ethylene glycol), poly(epsilon-caprolactone)-poly(ethylene glycol), and poly(hexadecylcyanoacrylate-co-poly(ethylene glycol)cyanoacrylate).

In some embodiments, the polymer can include one or more grafted moieties, e.g., alkyl chains of 4 to 18 carbons, such as a grafted butyl group. In some embodiments, such grafted moieties can enhance the solubility of the polymer in the process solvent and/or the stability of the polymeric nanoparticles formed in the subsequent steps.

In some embodiments, a single agent is attached to a single polymer, e.g., to a terminal end of the polymer. In some embodiments, a plurality of agents are attached to a single polymer (e.g., 2, 3, 4, 5, 6, or more). In some embodiments, the agents are the same agent. In some embodiments, the agents are different agents. In some embodiments, the agent is a therapeutic agent or an imaging agent.

In some embodiments, the therapeutic agent is an anti-neoplastic agent. In some embodiments, the anti-neoplastic agent is an alkylating agent, a vascular disrupting agent, a microtubule targeting agent, a mitotic inhibitor, a topoisomerase inhibitor, an anti-angiogenic agent or an anti-metabolite. In some embodiments, the anti-neoplastic agent is a taxane (e.g., paclitaxel, docetaxel, larotaxel or cabazitaxel). In some embodiments, the anti-neoplastic agent is an anthracycline (e.g., doxorubicin). In some embodiments, the anti-neoplastic agent is an epothilone (e.g., ixabepilone, epothilone B, epothilone D, BMS310705, dehydelone or ZK-epothilone). In some embodiments, the anti-neoplastic agent is a platinum-based agent (e.g., cisplatin). In some embodiments, the anti-neoplastic agent is a pyrimidine analog (e.g., gemcitabine).

In some embodiments, the anti-neoplastic agent is paclitaxel, attached to the polymer through the 2' or 7 carbon position, or both the 2' and 7 carbon positions. In some embodiments, the agent is linked to the polymer through the 7 position and has an acyl group at the 2' position (e.g., wherein the agent is a taxane such as paclitaxel, docetaxel, larotaxel or cabazitaxel).

In some embodiments, the anti-neoplastic agent is docetaxel. In some embodiments, the anti-neoplastic agent is docetaxel-succinate. In some embodiments, the anti-neoplastic agent is doxorubicin. In some embodiments, the anti-neoplastic agent is larotaxel. In some embodiments, the anti-neoplastic agent is cabazitaxel.

In some embodiments, the therapeutic agent is an agent for the treatment or prevention of cardiovascular disease. In some embodiments, the therapeutic agent is an agent for the treatment or prevention of an inflammatory or autoimmune disease.

In some embodiments, the agent is attached directly to the polymer, e.g., through a covalent bond. In some embodiments, the agent is attached to a terminal end of the polymer via an amide, ester, ether, amino, carbamate or carbonate bond. In some embodiments, the agent is attached to a terminal end of the polymer. In some embodiments, the polymer comprises one or more side chains and the agent is directly attached to the polymer through one or more of the side chains.

In some embodiments, a single agent is attached to a polymer. In some embodiments, multiple agents are attached to a polymer (e.g., 2, 3, 4 or more agents). In some embodiments, the agents are the same agent. In some embodiments, the agents are different agents.

In some embodiments, the agent is doxorubicin, and is covalently attached to the polymer through, e.g., an amide bond.

In some embodiments, the polymer-agent conjugate is:

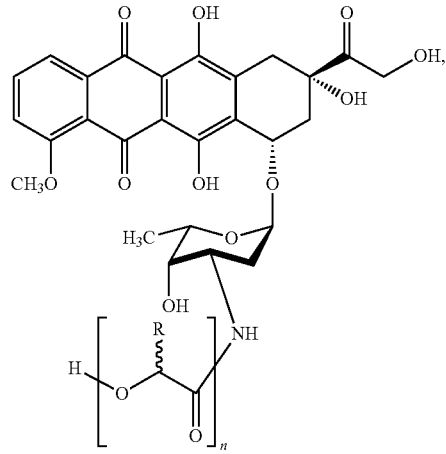

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the agent is paclitaxel, and is covalently attached to the polymer through, e.g., an ester bond.

In some embodiments, the polymer-agent conjugate is:

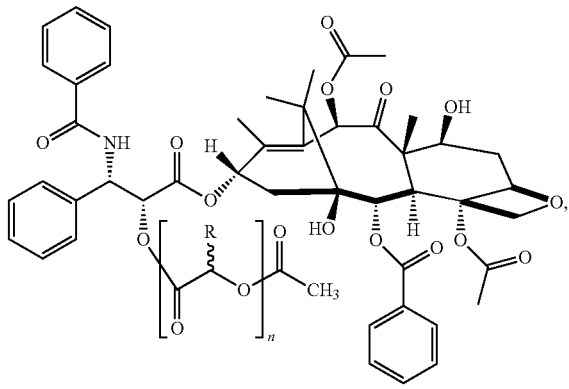

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer-agent conjugate is:

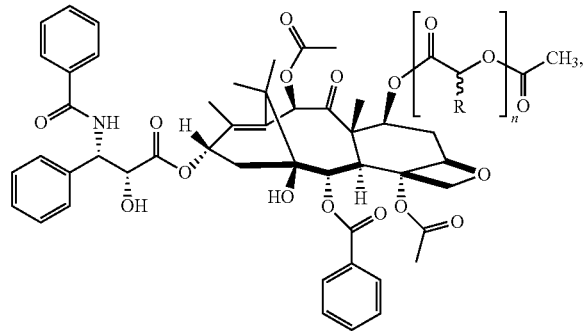

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the paclitaxel is attached through both the 2' and the 7 carbons. In some embodiments, the polymer-agent is provided as a mixture containing one or more or all of, drug-polymer species coupled through the 2' carbon, drug-polymer species coupled through the 7 carbon, and drug-polymer species coupled through both the 2' and the 7 carbons.

In some embodiments, the agent is paclitaxel, and is covalently attached to the polymer via a carbonate bond.

In some embodiments, the agent is docetaxel, and is covalently attached to the polymer through, e.g., an ester bond.

In some embodiments, the polymer-agent conjugate is:

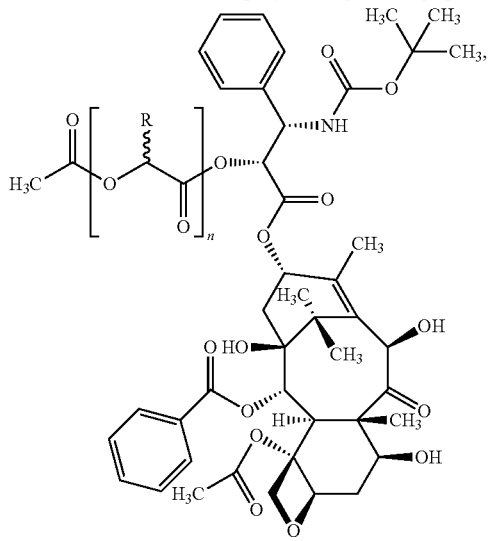

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer-agent conjugate is:

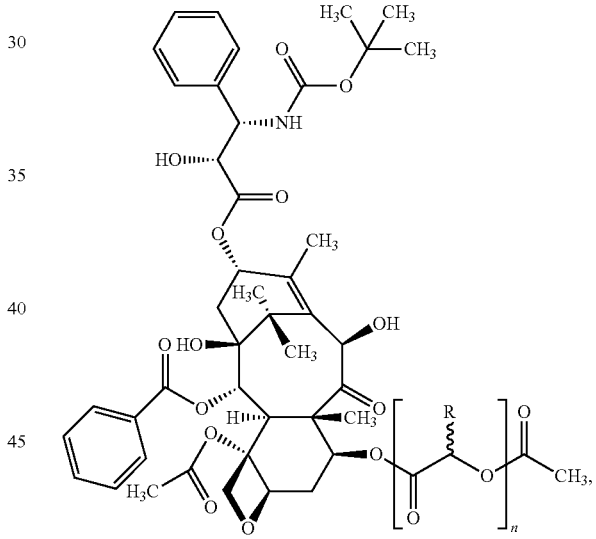

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the docetaxel is attached through both the 2' and the 7 carbons. In some embodiments, the polymer-agent is provided as a mixture containing one or more or all of, drug-polymer species coupled through the 2' carbon, drug-polymer species coupled through the 7 carbon, and drug-polymer species coupled through both the 2' and the 7 carbons.

In some embodiments, the agent is docetaxel, and is covalently attached to the polymer through a carbonate bond.

In some embodiments, the agent is attached to the polymer through a linker. In some embodiments, the linker is an alkanoate linker. In some embodiments, the linker is a PEG-based linker. In some embodiments, the linker comprises a disulfide bond. In some embodiments, the linker is a self-immolative linker. In some embodiments, the linker is an amino acid or a peptide (e.g., glutamic acid, branched glutamic acid or polyglutamic acid).

In some embodiments the linker is a multifunctional linker. In some embodiments, the multifunctional linker has 2, 3, 4 or more reactive moieties that may be functionalized with an agent. In some embodiments, all reactive moieties are functionalized with an agent. In some embodiments, not all of the reactive moieties are functionalized with an agent (e.g., the multifunctional linker has four reactive moieties, and only one, two or three react with an agent.)

In some embodiments, the polymer-agent conjugate is:

In some embodiments, two agents are attached to a polymer via a multifunctional linker. In some embodiments, the two agents are the same agent. In some embodiments, the two agents are different agents. In some embodiments, the agent is docetaxel, and is covalently attached to the polymer via a glutamate linker.

In some embodiments, the polymer-agent conjugate is:

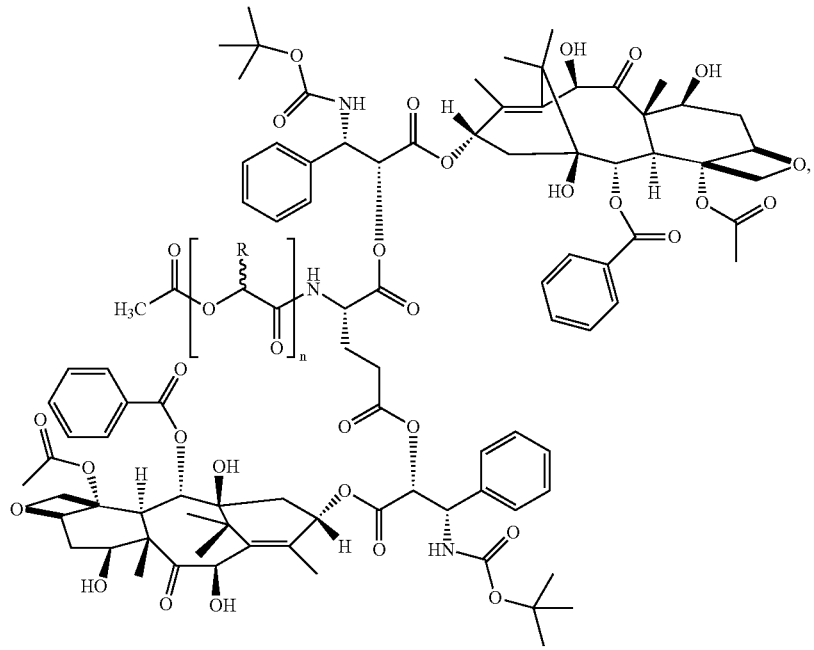

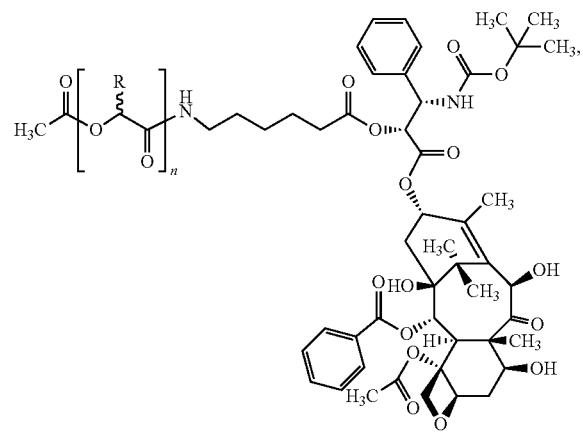

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, four agents are attached to a polymer via a multifunctional linker. In some embodiments, the four agents are the same agent. In some embodiments, the four agents are different agents. In some embodiments, the agent is docetaxel, and is covalently attached to the polymer via a bis(glutamate) linker.

In some embodiments, the polymer-agent conjugate is:

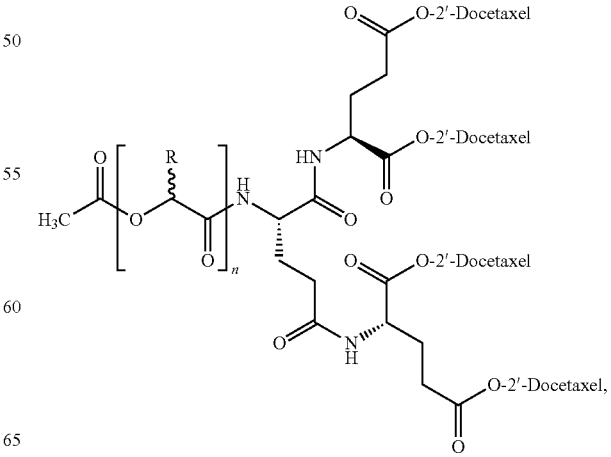

wherein 2'-docetaxel is:

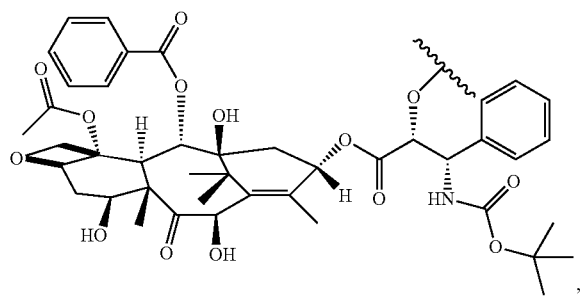

wherein about 40% to about 60% of R substituents are hydrogen (e.g., about 50%) and about 40% to about 60% are methyl (e.g., about 50%); and wherein n is an integer from about 90 to about 170 (e.g., n is an integer such that the molecular weight of the polymer-agent conjugate is from about 6 kDa to about 11 kDa).

In some embodiments, the polymer, e.g., the hydrophilic portion of an amphiphilic copolymer, comprises a terminal conjugate. In some embodiments, the terminal conjugate is a targeting agent or a dye. In some embodiments, the terminal conjugate is a folate or a rhodamine. In some embodiments, the terminal conjugate is a targeting peptide (e.g., an RGD peptide). By way of example, the targeting agent can be covalently linked to the polymer. In some embodiments, the targeting agent can be capable of binding to, or otherwise associating with, a target biological entity, e.g., a membrane component, a cell surface receptor, a prostate specific membrane antigen, or the like. In some embodiments, the targeting agent can cause the nanoparticles administered to a subject to become localized to a tumor, a disease site, a tissue, an organ, a type of cell, e.g., a cancer cell. In some embodiments, the targeting agent can be selected from the group of nucleic acid aptamers, growth factors, hormones, cytokines, interleukins, antibodies, integrins, fibronectin receptors, p-glycoprotein receptors, peptides and cell binding sequences.

In some embodiments, a radiopharmaceutical agent e.g., a radiotherapeutic agent, a radioimaging agent, or other radioisotope can be coupled to, associated with or incorporated in the polymer, e.g., embedded in the polymer.

In some embodiments, the process solvent is an organic solvent (or a mixture of two or more organic solvents). In some embodiments, the process solvent is capable of dissolving at least about 0.1%, or at least about 0.2%, by weight of the polymer at room temperature.

Some examples of suitable process solvents include, without limitation, acetone, ether, alcohol, tetrahydrofuran, 2-pyrrolidone, N-Methyl-2-pyrrolidone (NMP), dimethylformamide (DMF), dimethylacetamide (DMA), methyl acetate, ethyl formate, methyl ethyl ketone (MEK), methyl isobutyl ketone (MIBK), methyl propyl ketone, isopropyl ketone, isopropyl acetate, acetonitrile (MeCN) and dimethyl sulfoxide (DMSO).

In some embodiments, the anti-solvent can be an aqueous (water-based) solution, another solvent, a combination of a solvent and an aqueous solution, or a combination of one or more organic solvents. In some embodiments, the anti-solvent can be purified water. Some other examples of suitable anti-solvents include, without limitation, methanol, ethanol, n-propanol, isopropanol, n-butanol, ethyl ether, and water:ethanol (e.g., 50:50). In some cases, the anti-solvent can be a liquefied gas, such as carbon dioxide under adequate pressure.

In some embodiments, the anti-solvent can include a colloid stabilizer, e.g., to inhibit aggregation of the formed nanoparticles. Some examples of suitable colloid stabilizers include, without limitation, poly(vinyl alcohol) (PVA), Dextran and pluronic F68, poly (vinyl pyrrolidone), solutol, Tween 80, poloxamer, carbopol, poly-ethylene glycol (PEG), sodium dodecyl sulfate, poly (ε-caprolactone), peptides, and carbohydrates. Another example of a colloid stabilizers includes, without limitation, a PEG-lipid (e.g., PEG-ceramide, d-alpha-tocopheryl polyethylene glycol 1000 succinate, 1,2-Distearoyl-sn-Glycero-3-[Phospho-rac-(1-glycerol)] or lecithin). In some embodiments, the PVA is from about 5 to about 45 kDa, for example, the PVA is from about 5 to about 30 kDa (e.g., the PVA is from about 5 to about 20 kDa), and up to about 98% hydrolyzed (e.g., about 85% hydrolyzed). In some embodiments, the viscosity of the PVA (4% PVA in water), measured by utilizing the falling ball method, is in a range of about 2.5 to about 6.5 mPasec (e.g., in a range of about 2.5 to about 3.5 mPasec at a temperature of about 20° C.). In some embodiments, the viscosity of the PVA (4% PVA in water), measured by utilizing the falling ball method, is in a range of about 3.4 to about 4.6 mPasec.

In some embodiments, the polymer solution can have one or more additive molecules. As discussed above, in some embodiments, the additive molecules are embedded in the polymer prior to formation of the polymer solution. In other embodiments, the additive molecules can become embedded in the polymeric nanoparticles during the precipitation process. For example, in some embodiments, the additive molecule can be conjugated to the polymer, e.g., via covalent bonding, and the conjugated polymer can be dissolved in a process solvent to form the polymer solution. In other cases, the additive molecules can be present in the polymer solution without being conjugated to the polymer and become subsequently trapped in polymeric nanoparticles during the precipitation process.

By way of example, the additive molecules can be a therapeutic, or an imaging agent or a combination of therapeutic and imaging agents. Some examples of suitable therapeutic agents include, without limitation, anti-neoplastic agents, anti-inflammatory agents, cardiovascular active agents, and anti-metabolites.

In some embodiments, the imaging agent can be coupled, e.g., conjugated to the polymer, for incorporation in the nanoparticles. In other embodiments, the imaging agent can be coupled, e.g., via a chelating agent, to a therapeutic agent, which is in turn coupled, e.g., conjugated, to the polymer. The imaging agents can include, e.g., radioactive, non-radioactive, or fluorescent labels. Some examples of imaging agents include, without limitation, radiopharmaceuticals such as Technetium Bicisate, Ioxaglate, and Fluorodeoxyglucose, label-free Raman imaging agents, encapsulate MRI contrast agent Gd-DTPA, and rhodamine 6G as a fluorescent agent. In some embodiments, the imaging agent can be radiolabeled docetaxel (e.g., 3H-radiolabeled or 14C-radiolabeled docetaxel), or radiolabeled paclitaxel.

In some embodiments, the average particle size ($Z_{ave}$) can be equal to or less than about 500 nm. For example, the polymeric nanoparticles can exhibit an average particle size in a range of about 5 nm to about 500 nm, or in a range of about 10 nm to about 500 nm, or in a range of about 20 nm to about 500 nm, or in a range of about 30 nm to about 500 nm, or in a range of about 40 nm to about 500 nm, or in a range of about 50 nm to about 500 nm. In some embodiments, the average particle size ($Z_{ave}$) can be equal to or less than about 400 nm. For example, the polymeric nanoparticles can exhibit an average particle size in a range of about 5 nm to about 400 nm, or in a range of about 10 nm to about 400 nm, or in a range of about 20 nm to about 400 nm, or in a range of about 30 nm to about 400 nm, or in a range of about 50 nm to about 400 nm. In some embodiments, the average particle size ($Z_{ave}$) can be equal to or less than about 300 nm. For example, the polymeric nanoparticles can exhibit an average particle size in range of about 5 nm to about 300 nm, or in a range of about 10 nm to about 300 nm, or in a range of about 20 nm to about 300 nm, or in a range of about 40 nm to about 300 nm, or in a range of about 50 nm to about 300 nm.

In some embodiments, the average particle size ($Z_{ave}$) of the nanoparticles can be equal to or less than about 200 nm (e.g., equal to or less than about 195 nm (and, e.g., equal to or greater than about 20 nm), equal to or less than about 190 nm (and, e.g., equal to or greater than about 20 nm), equal to or less than about 185 nm (and, e.g., equal to or greater than about 20 nm), equal to or less than about 180 nm (and, e.g., equal to or greater than about 20 nm), equal to or less than about 175 nm (and, e.g., equal to or greater than about 20 nm), equal to or less than about 170 nm (and, e.g., equal to or greater than about 20 nm), equal to or less than about 165 nm (and, e.g., equal to or greater than about 20 nm), equal to or less than about 160 nm (and, e.g., equal to or greater than about 20 nm), equal to or less than about 155 nm (and, e.g., equal to or greater than about 20 nm), equal to or less than about 150 nm (and, e.g., equal to or greater than about 20 nm), equal to or less than about 145 nm (and, e.g., equal to or greater than about 20 nm), equal to or less than about 140 nm (and, e.g., equal to or greater than about 20 nm), equal to or less than about 135 nm (and, e.g., equal to or greater than about 20 nm), equal to or less than about 130 nm (and, e.g., equal to or greater than about 20 nm), equal to or less than about 125 nm (and, e.g., equal to or greater than about 20 nm), equal to or less than about 120 nm (and, e.g., equal to or greater than about 20 nm), equal to or less than about 115 nm (and, e.g., equal to or greater than about 20 nm), equal to or less than about 110 nm (and, e.g., equal to or greater than about 20 nm), equal to or less than about 105 nm (and, e.g., equal to or greater than about 20 nm), equal to or less than about 100 nm (and, e.g., equal to or greater than about 20 nm), equal to or less than about 95 nm (and, e.g., equal to or greater than about 20 nm), equal to or less than about 90 nm (and, e.g., equal to or greater than about 20 nm), equal to or less than about 85 nm (and, e.g., equal to or greater than about 20 nm), equal to or less than about 80 nm (and, e.g., equal to or greater than about 20 nm), equal to or less than about 75 nm (and, e.g., equal to or greater than about 20 nm), equal to or less than about 70 nm (and, e.g., equal to or greater than about 20 nm), equal to or less than about 65 nm (and, e.g., equal to or greater than about 20 nm), equal to or less than about 60 nm (and, e.g., equal to or greater than about 20 nm), equal to or less than about 55 nm or 50 nm (and, e.g., equal to or greater than about 20 nm)). For example, the average particle size can be in a range of about 50 nm to about 200 nm, or in a range of about 100 nm to about 200 nm.

In some embodiments, the nanoparticles generated by the above process exhibit a polydispersity index equal to or less than about 0.25. By way of example, the nanoparticles can exhibit a polydispersity index in a range of about 0.05 to about 0.1.

Further details regarding such methods, and associated systems, for generating polymeric nanoparticles can be found in commonly-owned co-pending patent application entitled "Methods and Systems for Generating Nanoparticles," having a Ser. No. 61/317,783 and filed on Mar. 26, 2010, which is hereby incorporated by reference in its entirety.

Figure 2:
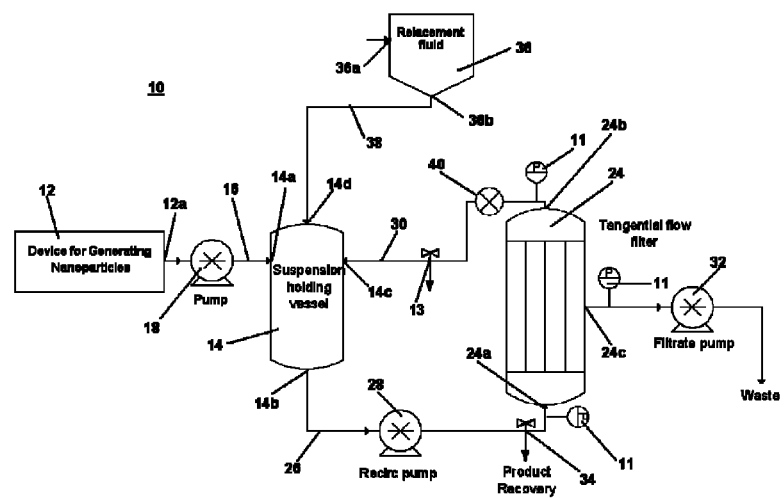

FIG. 2 schematically depicts a system 10 according to an embodiment of the invention for generating nanoparticles, which includes a device 12 for generating nanoparticles. In this embodiment, the device 12 generates a fluid stream in which the nanoparticles are contained, where the nanoparticle-containing fluid stream exits the device 12 via an output port 12a thereof. The device 12 can generate nanoparticles in a variety of ways. By way of example, as discussed in more detail below, in some embodiments the device 12 can generate nanoparticles by introducing a polymer solution into a flowing stream of an anti-solvent such that precipitation of polymeric nanoparticles occurs, e.g., in a manner discussed in more detail below.

The device 12 for generating nanoparticles is in fluid communication with a holding vessel 14. More specifically, in this exemplary implementation, the output port 12a of the device 12 is connected via a fluid passage 16 to an input port 14a of the holding vessel to allow the flow of a nanoparticle-containing fluid stream generated by the device 12 into the holding vessel. A pump 18 can be optionally used to facilitate the delivery of the nanoparticle-containing fluid stream into the holding vessel. In some implementations, the fluid passage 16 allows a continuous flow of the nanoparticle-containing fluid into the holding vessel 14.

Figure 3:
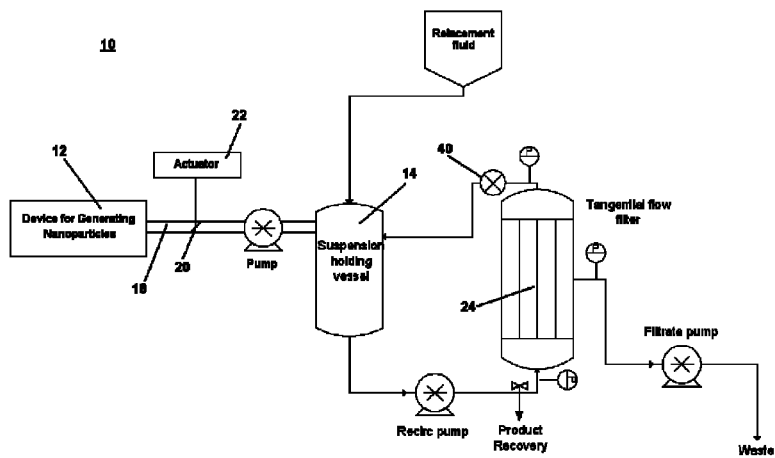

In other implementations, the fluid passage 16 can be configured to allow an intermittent flow of the nanoparticle-containing fluid into the holding vessel 14. By way of example, FIG. 3 schematically depicts such an implementation of the system 10 in which the fluid passage 16 includes an actuatable valve 20 that allows controlling the passage of the nanoparticle-containing fluid from the nanoparticle-generating device 12 to the holding vessel 14. For example, an actuator 22 that is electrically coupled to the valve 20 can periodically open the valve 20 to allow an intermittent flow of the fluid into the holding vessel 14.

Referring again to FIG. 2, the holding vessel 14 is in fluid communication with a filtration module 24 in a closed-loop configuration. More specifically, an output port 14b of the holding vessel 14 is connected via a fluid passage 26 to an input port 24a of the filtration module 24. In this implementation, a pump 28 (such as a gear pump or a peristaltic pump) is provided between the holding vessel 14 and the filtration module 24 to facilitate extracting at least a part of a nanoparticle-containing fluid accumulated in the holding vessel 14 and transferring it to the filtration module 24.

The nanoparticle-containing fluid transferred to the filtration module 24 passes through the module 24 to be separated into a nanoparticle-containing retentate and permeate. As noted above, a variety of filtration modules can be employed. By way of example, the filtration module 24 can provide tangential flow filtration of the nanoparticle-containing fluid passing therethrough.

With continued reference to FIG. 2, the nanoparticle-containing retentate exits the filtration module 24 through an exit port 24b thereof. A return fluid path 30 connects the exit port 24b of the filtration module 24 to another input port 14c of the holding vessel 14 to allow the fluid-containing retentate, or at least a portion thereof, to be returned to the holding vessel 14.

Another output port 24c of the filtration module 24 in turn allows draining the permeate out of the filtration module 24. In this implementation, a pump 32 that is fluidly coupled to the output port 24c of the filtration module 24 facilitates the extraction of the permeate out of the filtration module. The pump 32 can be utilized to adjust the flow rate of the permeate out of the filtration module, e.g., to ensure the rate of removal of the permeate out of the filtration module matches the flow rate of the nanoparticle-containing fluid into the holding vessel. Alternatively, the flow rate of the permeate out of the filtration module can be controlled by adjusting the flow rate of the retentate out of the filtration module (e.g., by restricting the flow of the retentate out of the filtration module). For example, a valve 40 disposed in the return fluid path 30 can allow controlling the flow rate of the retentate exiting the filtration module 24 and returning to the holding vessel 14. In some cases, the valve 40 can be employed to generate a back pressure on the filtration module.

A drainage or product recovery port 34 coupled to the fluid passage connecting the output port 14b of the holding vessel 14 to the input port 24a of the filtration module can be utilized to drain and collect the nanoparticle-containing fluid accumulated in the holding vessel, e.g., after a desired concentration and purity of the nanoparticles is achieved in the holding vessel or after removal of organic solvent(s) and the colloid stabilizer.

With continued reference to FIG. 2, in some embodiments the system 10 can include a reservoir 36 for containing a replacement fluid, such as deionized water. The reservoir 36 is in fluid communication with the holding vessel 14 via a fluid passage 38, which provides a fluid path from an output port 36b of the reservoir 36 to an input port 14d of the holding vessel. The reservoir 36 can also include an input port 36a that allows replenishing the replacement fluid contained therein. As discussed in more detail below, in some embodiments, the replacement fluid from the reservoir 36 can be made to flow into the holding vessel 14 once a desired concentration of the nanoparticles is achieved in the holding vessel 14 to commence a diafiltration process, for example, to remove organic solvent(s) present in the nanoparticle-containing fluid accumulated in the holding vessel 14.

The system 10 can also include one or more pressure gauges 11 for monitoring the pressure at various points, such as the input port 24a, the exit port 24b, and the output port 24c of the filtration module 24. Further, a valve 13 can be optionally provided in the return fluid path 30 between the exit port 24b of the filtration module and the input port 14c of the holding vessel 14 (typically after the pressure gauge that is disposed in proximity of the exit port 24b). In some cases, the valve 13 can be employed, e.g., to drain a portion of the nanoparticle-containing retentate exiting the filtration module.

In some embodiments, in use, a nanoparticle-containing flowing stream generated by the device 12 is introduced into the holding vessel 14 via its input port 14a while the fluid passage between the holding vessel 14 and the reservoir 16 is shut off. In some embodiments, the output port 14b of the holding vessel is initially shut off and remains closed for a certain amount of time as the nanoparticle-containing fluid is introduced into the holding vessel so that a desired volume of the fluid is accumulated into the holding vessel. Subsequently, the output port 16b is opened so that a portion of the accumulated fluid begins to flow from the holding vessel to the filtration module while the nanoparticle-containing fluid stream continues to enter the holding vessel via its input port 14a. Alternatively, the output port 14b of the holding vessel 14 is open as the nanoparticle-containing fluid begins to enter the holding vessel 14 via its input port 14a. The fluid flows from the holding vessel to the filtration module and passes through the module to be separated into a permeate that flows out of the output port 24c of the module and a retentate that flows out of the output port 24b of the filtration module. The retentate then flows through the fluid return path 30 into the holding vessel via its input port 14c. Once the flow of the retentate into the holding vessel is established, a steady state can be obtained during which the nanoparticle-containing fluid enters the holding vessel while a portion thereof is extracted to flow through the filtration module with the retentate returning to the holding vessel. In some embodiments, the filtration process can continue until a desired concentration of the nanoparticle-containing fluid is achieved in the holding vessel.

In some embodiments, the extraction of the nanoparticle-containing fluid from the holding vessel for passing through the filtration module continues for some time after the introduction of the nanoparticle-containing fluid into the holding vessel is terminated. Alternatively, the introduction of the nanoparticle-containing fluid and the extraction of the nanoparticle-containing fluid from the holding vessel can be terminated at the same time. Yet in other embodiments, the nanoparticle containing fluid stream can continue to flow into the holding vessel for some time after the extraction of the nanoparticle-containing fluid from the holding vessel is terminated, e.g., by shutting off the output port 14b of the holding vessel. Once a desired concentration of the nanoparticles in the holding vessel 14 is achieved and the flow of the nanoparticle-containing fluid from the device 12 into the holding vessel is terminated, a fluid flow can be established, via the fluid passage 38, between the holding vessel 14 and the reservoir 36 in which a replacement fluid (e.g., deionized water) is contained such that the holding vessel receives, via its input port 14d, a flow of the replacement fluid. Further, a flow can be established between the holding vessel, via its output portion 14b, and the filtration module 24 (which can be the same module as that utilized in the previous stage or a different module). In some cases, the flow of the replacement fluid into the holding vessel starts prior to establishing a flow between the holding vessel and the filtration module. In other cases, the fluid flow between the holding vessel and the filtration module starts prior to starting the fluid flow between the reservoir 36 and the holding vessel. Yet in other cases, the fluid flow between the reservoir 36 and the holding vessel 14 is established at the same time as the fluid flow between the holding vessel and the filtration module 24. The passage of the fluid through the filtration module 24 can result in removal of the organic solvent(s) and the colloid stabilizer, if any, in the fluid as a permeate with the nanoparticle-containing retentate returning to the holding vessel 14 via the fluid passage 30.

This filtration cycle can be repeated until a desired aqueous solution of the nanoparticles is achieved in the holding vessel 14. In some cases, the filtration cycle can continue for some time after the flow of the replacement fluid from the reservoir 36 to the holding vessel is terminated. Alternatively, the flow of the replacement fluid from the reservoir 36 to the holding vessel can continue for some time after the filtration cycle is terminated. Yet in other cases, the flow of the replacement fluid from the reservoir 36 to the holding vessel and the filtration cycle can be terminated at the same time. In some embodiments, the rate of flow of the replacement fluid into the holding vessel can be substantially equal to the rate at which the permeate is drained from the filtration module. In this manner, the concentration of the nanoparticles in the holding vessel remains substantially constant during the diafiltration process. Alternatively, the rate of flow of the replacement fluid into the holding vessel can be less or greater than the rate at which the permeate is drained from the filtration module.

As noted above, in some embodiments, the nanoparticle-generating device generates nanoparticles contained in a fluid stream by introducing an anti-solvent into a static mixer to create a mixed flowing stream of the anti-solvent and introducing a polymer-carrying liquid, e.g., a polymer solution, or a polymer dispersion or a mixed polymer solution/dispersion, into the mixed flowing stream of an anti-solvent so as to form polymeric nanoparticles. The polymeric nanoparticles can be formed via aggregation (e.g., assembly/growth) of at least one polymer, and in some cases one or more additives, of the polymer solution, or of the polymer dispersion or of the mixed polymer solution/dispersion, as well as in some embodiments a colloid stabilizer of the anti-solvent. In some embodiments, one or more components of the nanoparticles can be covalently or non-covalently bound.

Figure 4:
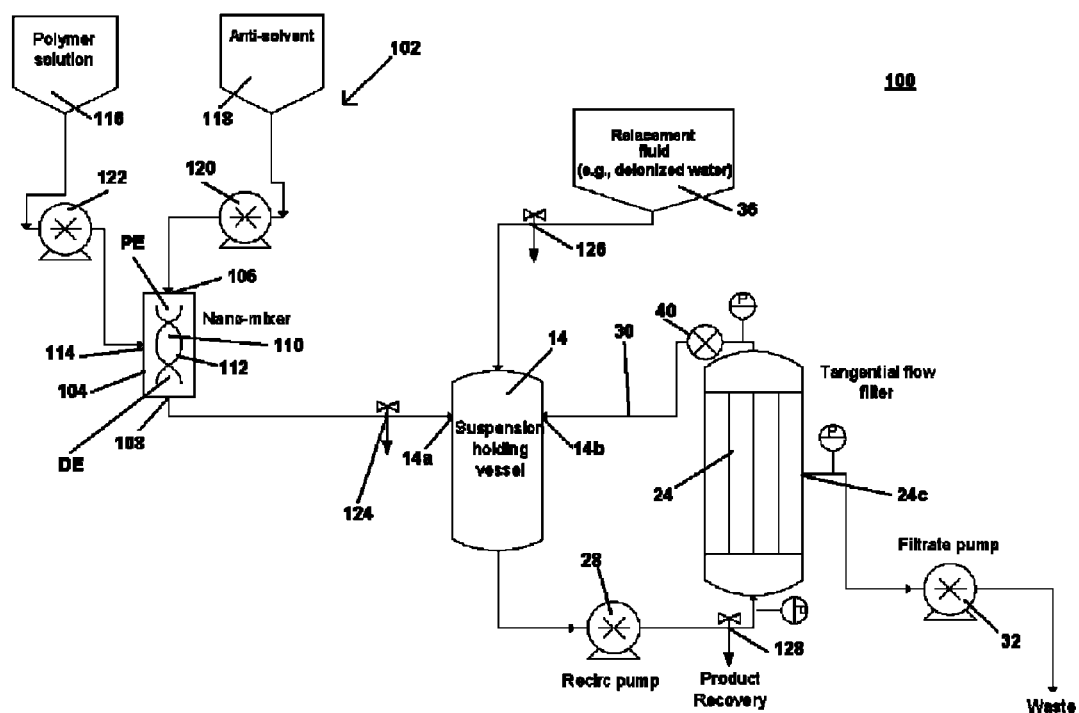

FIG. 4 schematically illustrates a system 100 according to an embodiment of the invention for generating nanoparticles in which a nanoparticle-generating device 102 generates polymeric nanoparticles by introducing a polymer-carrying liquid into a mixed anti-solvent flowing stream. More specifically, the nanoparticle-generating device 102 can include a conduit 104, e.g., a hollow tube, that extends axially from a first input (inlet) port 106, through which a fluid, e.g., an anti-solvent, can be introduced into the conduit, and an output (outlet) port 108. A static mixer 110 is disposed in the conduit to receive the fluid entering the conduit through the input port 106. The exemplary static mixer 110 extends from a proximal end (PE) to a distal end (DE), and includes a plurality of stationary baffles 112 that cause mixing of the fluid as it flows through the mixer. Different types of static mixers can be employed in the device 102. By way of example, static mixers disclosed in U.S. Pat. Nos. 3,286,992 and 4,511,258 entitled, respectively, "Mixing Device," and "Static Material Mixing Apparatus," which are herein incorporated by reference in their entirety, can be employed. By way of another example, in some embodiments, static mixers marketed by Chemineer, Inc. of Ohio, U.S.A. under the trade designation Kenics static mixers can be employed.

The device 102 further includes a second input port 114 through which a second fluid (e.g., another fluid such as a polymer solution as discussed below) can be introduced into the fluid flowing axially along the conduit 104 through the static mixer 110. In this embodiment, the second input port 114 is disposed at an intermediate location between the proximal end (PE) and the distal end (DE) of the static mixer 110.

In this implementation, the device 102 includes a reservoir 116 for storing a polymer solution and a reservoir 118 for storing an anti-solvent. The reservoir 118 is fluidly coupled via a pump 120 to the input port 106 and the reservoir 116 is fluidly coupled via a pump 122 to the input port 114 of the conduit The output port 108 of the conduit 104 is fluidly coupled to the input 14a of the holding vessel 14 to allow a fluid stream containing nanoparticles exiting the conduit 104 to flow into the holding vessel 14. The holding vessel 14 is coupled to the filtration module 24 in a closed-loop configuration as discussed above in the connection with the previous embodiment.

In use, an anti-solvent flowing stream is established through the conduit 104 via the input port 106 by causing the anti-solvent to flow from the reservoir 118 into the conduit via the pump 120. The fluid passage between the holding vessel 14 and the reservoir 36 for storing the replacement fluid is shut off during this stage of generating and filtering the nanoparticle-containing fluid. As discussed in more detail below, in many embodiments the replacement fluid is employed in subsequent filtration steps after the generation of the nanoparticle-containing fluid and its concurrent filtration are completed. The static mixer 110 causes mixing of the flowing anti-solvent so as to provide a mixed flowing stream of the anti-solvent before the stream reaches the second input port 114. Once a mixed flowing stream of the anti-solvent has been established, a polymer solution stored in the reservoir 116 can be introduced into the anti-solvent stream via the second input port 114 by causing the polymer solution to flow from the reservoir 116 into the conduit via the pump 122.

The contact of the polymer solution with the anti-solvent results in precipitation of the polymer into a plurality of polymeric nanoparticles that are carried by the stream of the anti-solvent away from the static mixer 110. In many embodiments, the rate of flow of the anti-solvent through the conduit 104 is substantially greater than the flow rate of the polymer solution into the conduit, e.g., by a factor of about 10 or more. Hence, in such embodiments, the nanoparticles are surrounded primarily by the anti-solvent—including any additive(s) such as a colloid stabilizer added to the anti-solvent— as they move down the conduit to the output port 108. Further, in many embodiments, the flow rate of the anti-solvent is sufficiently fast to ensure that the polymer solution entering the conduit would interact with a fresh batch of anti-solvent that is substantially free of process solvent and polymeric material that had previously entered the conduit.

The formed nanoparticles exit the output port of the conduit as a suspension in a fluid stream comprising a mixture of anti-solvent and the process solvent. The holding vessel 14 receives the nanoparticle-containing fluid stream via its input port 14a. Concurrent with the flow of the nanoparticle-containing fluid stream into the holding vessel 14, a portion of the nanoparticle-containing fluid accumulated in the holding vessel is extracted from the holding vessel 14 through its output port 14b via the recirculation pump 28 to flow to the filtration module 24.

The passage of the nanoparticle-containing fluid through the filtration module results in the formation of a nanoparticle-containing retentate and a permeate. The permeate (filtrate) is drained from the filtration module via the output port 24c. The filtrate pump 32 (e.g., a gear pump or a peristaltic pump) facilitates the removal of the permeate from the filtration module. The retentate, which has a higher concentration of the nanoparticles than the nanoparticle-containing fluid entering the filtration module, returns to the holding vessel via the fluid return path 30.

In many embodiments, the drainage rate of the permeate from the filtration module is set to be substantially the same as the flow rate of the nanoparticle-containing fluid generated by the device 102 into the holding vessel 14. For example, this can be achieved by adjusting the flow rate of the pump 32 to match the combined flow rates of the pumps 122 and 120. In this manner, a steady-state volume of the nanoparticle-containing fluid in the holding vessel 14 can be achieved that remains substantially constant while the nanoparticle-containing fluid is generated and filtered.

The filtration cycle can continue as more nanoparticle-containing fluid generated by the device 102 enters the holding vessel 14. In many implementations, the filtration cycle can continue until the anti-solvent and process solution stored in the reservoir 116 and 118 are depleted. In some cases, even after the depletion of the anti-solvent and the process solution, the filtration cycle can continue until a desired concentration of the nanoparticles is achieved in the holding vessel 14.

Subsequently, the concentrated nanoparticle-containing fluid in the holding vessel is subjected to a diafiltration process to remove organic solvent(s), colloid stabilizer (e.g., PVA) and unincorporated polymer, if any, present in the fluid. More specifically, the fluid passage between the nanoparticle-generating device 102 and the holding vessel 14 can be shut off via the valve 124, and a fluid flow can be established between the reservoir 36 in which a replacement fluid (e.g., deionized water) is stored and the holding vessel 14 by opening the valve 126. As the replacement fluid (e.g., deionized water) flows into the holding vessel 14, the fluid accumulated in the holding vessel is passed through the filtration module 24 (which can be the same module as that utilized in the previous stage or a different module). The passage of the fluid through the filtration module 24 results in removal of the organic solvent(s) and the colloid stabilizer in the fluid as a permeate with the nanoparticle-containing retentate returning to the holding vessel 14. The permeate is drained from the filtration module. This filtration cycle can be repeated until a desired aqueous solution of the nanoparticles is achieved in the holding vessel 14. In some embodiments, the rate of flow of the replacement fluid into the holding vessel can be substantially equal to the rate at which the permeate is drained from the filtration module. In this manner, the concentration of the nanoparticles in the holding vessel remains substantially constant during the diafiltration process. Alternatively, the rate of flow of the replacement fluid into the holding vessel can be less or greater than the rate at which the permeate is drained from the filtration module.

Subsequently, the aqueous nanoparticle-containing fluid accumulated in the holding vessel 14 can be collected via the product recovery valve 128. The collected nanoparticle-containing fluid can be further filtered to generate a nanoparticle suspension having a greater concentration of the nanoparticles. In some cases, a lyoprotectant can be added to the concentrated nanoparticle suspension, which can then be stored into vials and lyophilized.

The above methods and systems for generating nanoparticles provide a number of advantages. For example, the systems of the invention can present a reduced foot-print relative to conventional systems, and can require fewer components (e.g., fewer holding vessels) and hence a lower capital expense. Further, the methods of the invention can improve efficiency of generating nanoparticles. In particular, as noted above, the holding vessel is coupled to both the nanoparticle-generating device and the filtration module to perform the filtration step concurrently with the step of generating the nanoparticles. This allows utilizing a smaller holding vessel than in systems in which the generation of a nanoparticle-containing fluid and its filtration are performed sequentially. By way of example, in some implementations of the above system 100, the volume of the holding vessel 14 can be at least 10 times less than the combined volumes of the reservoirs 116 and 118 used to store the anti-solvent and the polymer solution. Further, as noted above, the methods and systems can reduce the processing time for generating nanoparticles.

The following Example is provided to further elucidate various aspects of the invention. The Example is provided for illustrative purposes only and not to necessarily indicate the optimal ways of practicing the invention or the optimal results that can be obtained.

EXAMPLE

A system based on the system shown in FIG. 4 above was assembled to generate polymeric nanoparticles contained in a fluid and to filter the nanoparticle-containing fluid concurrently with the generation of the nanoparticles.

The polymeric nanoparticles were generated via nanoprecipitation by introducing a polymer solution into a mixed flowing anti-solvent. Separate glass reservoirs containing a polymer solution and an aqueous polyvinyl alcohol (PVA) (anti-solvent) solution were, respectively, connected via pre-calibrated magnetically driven gear pumps (Ismatec, Cole-Parmer) to a 5 mm helical mixing device.

A 5 mm ID helical mixer device was constructed by inserting a 5 mm OD polyacetal helical mixer (Cole-Parmer) into a 5 mm ID polypropylene tube fitted with a barbed polypropylene "Y" fitting on one end. The mixer was extended through one of the arms of the "Y" fitting. The aqueous phase (i.e., anti-solvent) was directed via ¼ inch tubing through the mixer-containing arm. The organic phase (i.e., polymer solution) was directed via ⅜ inch tubing through the other (empty) arm. A ¼ inch to ⅛ inch reducer was connected to the bottom port to provide a slight back pressure.

The outlet of the mixing device was connected to a suspension holding vessel (a 2-liter polysulfone reservoir). The holding vessel was coupled via a recirculation pump (Ismatec, Cole-Parmer) to a tangential flow filter (TFF) (GE Healthcare hollow fiber cartridge, polysulfone membrane, 500 kD NMWC, 0.48 m$^2$) and a return path was provided from a retentate output port of the filter to the holding vessel to form a TFF recirculation loop. The filtrate (permeate) outlet of the TFF was connected via a filtrate pump (Masterflex, Cole-Parmer) to waste. A replacement fluid (RODI water) vessel was also connected to the reservoir. All product contact connections were formed of polytetrafluoroethylene (PTFE), with the remaining being flexible PVC or PharmMed tubing.

Polymer and PVA (anti-solvent) solutions were prepared as follows: 6 grams of CPX1107 (docetaxel custom conjugated PLGA) (Mw: 9.8 kD, drug loading 7.6%, AMRI Albany, N.Y.) and 4 gm of 5050DL-PLGA mPEG2k (Mw: 11 kD) (Lakeshore Biomaterials, Birmingham, Ala.) were dissolved in one liter (L) of acetone. Separately, 11 L of 0.5% PVA was prepared by combining 1.1 L of previously prepared stock solution of 5% PVA with 9.9 L of RODI water. The stock solution was prepared by dissolving 110 gm of PVA (80% hydrolyzed, Mw: 9-10 kD, Sigma-Aldrich, St. Louis, Mo.) into 2200 ml of RODI water and heating to 80° C. for 3 hr. The solution was cooled to room temperature, filtered and stored at 4° C. Both polymer and PVA solutions were filtered through 0.2 μm filters prior to use.

The process began by initiating in sequence PVA solution flow followed by polymer solution flow. The PVA and polymer pump rates were set at 220 and 22 ml/min, respectively. The effluent from the mixer (~242 ml/min) was directed to the holding vessel. After approximately 1 L of nanoparticle suspension was collected, the recirculation pump was initiated at crossflow rate of ~3.7 L/min. Once recirculation was established, the filtrate pump was initiated at ~220-250 ml/min. Throughout the time course of the nanoprecipitating and concentrating, approximately 50 min, the level of fluid in the holding vessel was maintained at ~1 L and TFF pressure drop and trans-membrane pressure (TMP) remained stable. When the polymer solution tank was drained, the polymer pump was turned off followed by the PVA pump.

Diafiltration was initiated by disconnecting the input suspension line of the holding vessel, sealing the holding vessel and opening the replacement fluid line to allow the replacement fluid to flow into the holding vessel. Ten volume exchanges were processed. Once the diafiltration was complete, the suspension underwent a final concentration from ~1 L to ~250 ml and finally recovered.

Analysis of the final suspension indicated a 94% yield as measured by docetaxel content and particle sizes as measured by the Zetasizer (Malvern Instruments). Table 1 below lists Zave, PdI, Dv50, and Dv90 of the nanoparticles in the final suspension ($Z_{ave}$ and PdI were defined above; Dv50 is defined as the particle size below which the sizes of 50% of the particles lies; Dv90 is defined as the particle size below which the sizes of 90% of the particles lies.):

TABLE 1

| $Z_{avg}$ | PdI | Dv50 | Dv90 |
|---|---|---|---|
| 83.7 nm | .069 | 70.2 nm | 108 nm |

All publications referred to herein, including patents, published patent applications, articles, among others, are hereby incorporated by reference in their entirety.

Those having ordinary skill in the art will appreciate that various changes can be made to the above embodiments without departing from the scope of the invention.

What is claimed is:

1. A system for filtering nanoparticles contained in a fluid, comprising:
    a holding vessel adapted for receiving a nanoparticle-containing fluid stream at a flow rate in a range of about 20 ml/min to about 2000 ml/min,
    a filtration module fluidly connected to the vessel to receive at least a portion of a nanoparticle-containing fluid accumulated in the holding vessel to separate a nanoparticle-containing retentate from a permeate, and
    a return path providing a fluid passage for the nanoparticle-containing retentate to the holding vessel,
    wherein said holding vessel has a volume equal to or less than about 10 liters.

2. The system of claim 1, wherein said holding vessel has a volume in a range of about 1 liter to about 5 liters.

3. The system of claim 1, wherein said flow rate is in a range of about 250 ml/min to about 2000 ml/min.

4. The system of claim 1, further comprising a drainage port for removing said permeate from the filtration module.

5. The system of claim 4, further comprising a pump coupled to the drainage port for facilitating the removal of the permeate from the filtration module.

6. The system of claim 5, wherein said pump is configured to remove the permeate from the filtration module at a rate substantially equal to a rate at which the holding vessel receives the nanoparticle-containing fluid stream.

7. The system of claim 1, further comprising a reservoir for containing a replacement fluid, said reservoir being in fluid coupling with the vessel to provide a flow of the replacement fluid.

8. The system of claim 1, further comprising a pump for transferring the nanoparticle-containing fluid accumulated in the holding vessel to the filtration module.

9. The system of claim 1, wherein said filtration module provides tangential flow filtration (TFF).

10. The system of claim 1, further comprising a port for draining fluid accumulated in the holding vessel.

11. A system for generating nanoparticles, comprising:
    a device for generating a plurality of nanoparticles contained in a fluid stream flowing at a flow rate in a range of about 20 ml/min to about 2000 ml/min,
    a holding vessel in fluid communication with the device to receive the nanoparticle-containing fluid stream,
    a filtration module in fluid communication with the holding vessel to receive at least a portion of a nanoparticle-containing fluid accumulated in the vessel to separate a nanoparticle-containing retentate from a permeate,
    a return path providing a fluid passage for the nanoparticle-containing retentate to the holding vessel,
    wherein said holding vessel has a volume equal to or less than about 10 liters.

12. The system of claim 11, wherein said holding vessel has a volume in a range of about 1 liter to about 5 liters.

13. The system of claim 11, wherein said flow rate is in a range of about 250 ml/min to about 2000 ml/min.

14. The system of claim 11, wherein said filtration module comprises a port for removing said permeate therefrom.

15. The system of claim 11, further comprising a port for draining fluid accumulated in the holding vessel.

16. The system of claim 11, wherein said filtration module provides tangential flow filtration (TFF).

17. The system of claim 11, wherein said device for generating nanoparticles is configured to generate polymeric nanoparticles by introducing a polymer solution into a mixed flowing stream of an anti-solvent.

18. The system of claim 17, wherein said device comprises a reservoir for storing the polymer solution and a reservoir for storing the anti-solvent.

19. The system of claim 18, wherein a volume of said holding vessel is at least about 10 times less than a combined volume of said reservoir for storing the polymer solution and said reservoir for storing the anti-solvent.

20. The system of claim 17, wherein said device comprises a conduit having a first input port for receiving the anti-solvent, and at least one static mixer disposed in the conduit to generate a mixed flowing stream of the anti-solvent.

21. The system of claim 20, wherein said conduit further comprises a second input port disposed relative to the static mixer so as to allow introducing a polymer solution into the mixed flowing stream of the anti-solvent to generate polymeric nanoparticles.

* * * * *